(12) United States Patent
Nielsen et al.

(10) Patent No.: US 7,060,468 B2
(45) Date of Patent: Jun. 13, 2006

(54) THERMOSTABLE GLUCOAMYLASE

(75) Inventors: Bjarne Ronfeldt Nielsen, Virum (DK); Ruby Ilum Nielsen, Farum (DK); Jan Lehmbeck, Vekso (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/625,115

(22) Filed: Jul. 22, 2003

(65) Prior Publication Data

US 2004/0142434 A1 Jul. 22, 2004

Related U.S. Application Data

(60) Division of application No. 09/821,616, filed on Mar. 29, 2001, now Pat. No. 6,620,924, which is a continuation of application No. 09/199,290, filed on Nov. 24, 1998, now Pat. No. 6,255,084, which is a continuation-in-part of application No. 09/107,657, filed on Jun. 30, 1998, now abandoned, and a continuation-in-part of application No. 08/979,673, filed on Nov. 26, 1997, now abandoned.

(60) Provisional application No. 60/094,344, filed on Jul. 28, 1998, provisional application No. 60/070,746, filed on Jan. 8, 1998.

(30) Foreign Application Priority Data

Dec. 30, 1997 (DK) .................................. 1557/97
Jul. 10, 1998 (DK) ............................... 1998 00925

(51) Int. Cl.
*C12P 19/20* (2006.01)
*C12N 9/34* (2006.01)

(52) U.S. Cl. ........................................ 435/96; 435/205
(58) Field of Classification Search .................. 435/96, 435/205

See application file for complete search history.

(56) References Cited

U.S. PATENT DOCUMENTS

| 4,247,637 A | 1/1981 | Tamura et al. |
| RE32,153 E | 5/1986 | Tamura et al. |
| 4,587,215 A | 5/1986 | Hirsh |

FOREIGN PATENT DOCUMENTS

| EP | 0 135 138 A2 | 3/1985 |
| EP | 0 255 124 A2 | 2/1988 |
| WO | WO 86/01831 | 3/1986 |

OTHER PUBLICATIONS

H. Guo et al:, "Protein Tolerance to Random Amino Acid Change", PNAS 101(25): 9205-9210. (Jun. 2004).*
Abstract of Japanese Patent Application No. 60/145905 (Jul. 1985).
Abstract of Japanese Patent No. JP 63039577 A and Japanese Patent No. JP 92025794 B (Feb. 1988).
Hata et al., Agric. Biol. Chem., vol. 55, pp. 941-949 (1991).
Ventura et al., Applied and Environmental Microbiology, vol. 61, pp. 399-402 (1995).
Swiss-Prot Accension # AMVG-Aspor (Jun. 1994).
Derwent Geneseq Accension # Q04731 (Oct. 1990).
EMBL Accension No. D01035 (Oct. 1993).
EMBL Accension E03645 (Oct. 1997).
Derwent Genseq Accension No. 40212 (Jan. 1992).
L. Bunni et al., Enzyme Microb. Technology, 1989, vol. 11, Jun. pp. 370-375.

* cited by examiner

*Primary Examiner*—Rebecca Prouty

(74) *Attorney, Agent, or Firm*—Jason I. Garbell; Elias J. Lambiris

(57) ABSTRACT

The invention relates to starch conversion processes using glucoamylases derived from *Talaromyces emersonii* and related glucoamylases.

15 Claims, 10 Drawing Sheets

```
        10                 30                  60                 70                  90
ACGAGATGTGTATATACTGTGAACCAAACTAGATGATGTCAGTTATGCTGGTCTGAGAACTCATAGAAGCCCTTGAAAATACCCCAAGCT
                   110                130                 150                 170
AGCACTCCAACCCTAACTCTGTTGCTCTACTAGATCAAGACGAGTACTCTGATTGAGCTGCAGGCTTGGAATATATGATTAGCAGAAAAA
         190                210                 230                  250                 270
GGGTTAAAACTTGTATGACAATCAGTTTGTCAGTACTCCGTAGTGATGCCATGTCTATAGAGTCGACACTAAGGCAGCATGTGAATGAGT
                   290                310                 330                 350
CGGAAATGACAGGAAGCAGATTCCTTAACAGTCATGTTCTCCGTGCCTGCATCCCACGTCACCTGCAAAGATGCGACGCTACTCCACAC
         370                390                 410                 430                 450
CGGCGCCTTGATGTCTGCTGTTCCTGGCCTAGTGGAGCCCCATGCGCTGCTAGCTCGTGGTCTTCGAATAAATCAGAATAAAAAACGGAG
                   470                490                 510                 530
TAATTAATTGCGCCCGCAACAAACTAAGCAATGTAACTCAATGCCAAGCTTCCGCTGATGCTCTTGACATCTCCGTAGTGGCTTCTTTCG
         550                570                 590                 610                 630
TAATTTCAGACGTATATATAGTAGTAATGCCCAGCAGGCCGGGATAATGATGGGGATTTCTGAACTCTCTGCTTCCGTACGCTGAACAGT
                   650                670                 690                 710
TTGCTTGCGTTGTCAACCATGGCGTCCCTCGTTGCTGGCGCTCTCTGCATCCTGGGCCTGACGCCTGCTGCATTTGCACGAGCGCCCGTT
                    M  A  S  L  V  A  G  A  L  C  I  L  G  L  T  P  A  A  F  A  R  A  P  V
         730                750                 770                 790                 810
GCAGCGCGAGCCACCGGTTCCCTGGACTCCTTTCTCGCAACCGAAACTCCAATTGCCCTCCAAGGCGTGCTGAACAACATCGGGCCCAAT
  A  A  R  A  T  G  S  L  D  S  F  L  A  T  E  T  P  I  A  L  Q  G  V  L  N  N  I  G  P  N
                   830                850                 870                 890
GGTGCTGATGTGGCAGGAGCAAGCGCCGGCATTGTGGTTGCCAGTCCGAGCAGGAGCGACCCAAATgtaggttctttcccaccagaaat
 G  A  D  V  A  G  A  S  A  G  I  V  V  A  S  P  S  R  S  D  P  N
         910                930                 950                 970                 990
tacttatttaaatcagccctctgacaggttgaagATTTCTACTCCTGGACACGTGACGCAGCGCTCACGGCCAAATACCTCGTCGACGCC
                                    Y  F  Y  S  W  T  R  D  A  A  L  T  A  K  Y  L  V  D  A
         1010               1030                1050                1070
TTCATCGCGGGCAACAAGGACCTAGAGCAGACCATCCAGCAGTACATCAGCGCGCAGGCGAAGGTGCAAACTATCTCCAATCCGTCCGGA
 F  I  A  G  N  K  D  L  E  Q  T  I  Q  Q  Y  I  S  A  Q  A  K  V  Q  T  I  S  N  P  S  G
         1090               1110                1130                1150                1170
GATTTATCCACCGGTGGCTTAGGTGAGCCCAAGTTCAATGTGAATGAGACGGCTTTTACCGGGCCCTGGGGTCGTCCACAGAGGGACGGA
 D  L  S  T  G  G  L  G  E  P  K  F  N  V  N  E  T  A  F  T  G  P  W  G  R  P  Q  R  D  G
                   1190               1210                1230                1250
CCAGCGTTGAGAGCGACGGCCCTCATTGCGTATGCGAACTATCTCATCgtaagcttctgctcgctgcccttctctctgctcgtatgctaa
 P  A  L  R  A  T  A  L  I  A  Y  A  N  Y  L  I
         1270               1290                1310                1330                1350
gtagtcctgtcagGACAACGGCGAGGCTTCGACTGCCGATGAGATCATCTGGCCGATTGTCCAGAATGATCTGTCCTACATCACCCAATA
              D  N  G  E  A  S  T  A  D  E  I  I  W  P  I  V  Q  N  D  L  S  Y  I  T  Q  Y
                   1370               1390                1410                1430
CTGGAACTCATCCACCTTCGgtaggcaaatgaatattcccgacacagcgtggtactaatttgattcagACCTCTGGGAAGAAGTAGAAGG
 W  N  S  S  T  F                                                    D  L  W  E  E  V  E  G
         1450               1470                1490                1510                1530
```

FIG 5A

```
ATCCTCATTCTTCACAACCGCCGTGCAACACCGCGCCCTGGTCGAAGGCAATGCACTGGCAACAAGGCTGAACCACACGTGCTCCAACTG
 S  S  F  F  T  T  A  V  Q  H  R  A  L  V  E  G  N  A  L  A  T  R  L  N  H  T  C  S  N  C
         1550              1570              1590              1610
CGTCTCTCAGGCCCCTCAGGTCCTGTGTTTCCTGCAGTCATACTGGACCGGATCGTATGTTCTGGCCAACTTTGGTGGCAGCGGTCGTTC
 V  S  Q  A  P  Q  V  L  C  F  L  Q  S  Y  W  T  G  S  Y  V  L  A  N  F  G  G  S  G  R  S
    1630              1650              1670              1690              1710
CGGCAAGGACGTGAATTCGATTCTGGGCAGCATCCACACCTTTGATCCCGCCGGAGGCTGTGACGACTCGACCTTCCAGCCGTGTTCGGC
 G  K  D  V  N  S  I  L  G  S  I  H  T  F  D  P  A  G  G  C  D  D  S  T  F  Q  P  C  S  A
         1730              1750              1770              1790
CCGTGCCTTGGCAAATCACAAGGTGGTCACCGACTCGTTCCGGAGTATCTATGCGATCAACTCAGGCATCGCAGAGGGATCTGCCGTGGC
 R  A  L  A  N  H  K  V  V  T  D  S  F  R  S  I  Y  A  I  N  S  G  I  A  E  G  S  A  V  A
    1810              1830              1850              1870              1890
AGTCGGCCGCTACCCTGAGGATGTCTACCAGGGCGGGAACCCCTGGTACCTGGCCACAGGAGCGGCTGCAGAGCAGCTTTACGACGCCAT
 V  G  R  Y  P  E  D  V  Y  Q  G  G  N  P  W  Y  L  A  T  A  A  A  E  Q  L  Y  D  A  I
         1910              1930              1950              1970
CTACCAGTGGAAGAAGATCGGCTCGATAAGTATCACGGACGTTAGTCTGCCATTTTTCCAGGATATCTACCCTTCTGCCGCGGTGGGCAC
 Y  Q  W  K  K  I  G  S  I  S  I  T  D  V  S  L  P  F  F  Q  D  I  Y  P  S  A  A  V  G  T
    1990              2010              2030              2050              2070
CTATAACTCTGGCTCCACGACTTTCAACGACATCATCTCGGCCGTCCAGACGTATGGTGATGGATATCTGAGTATTGTCgtacgttttgc
 Y  N  S  G  S  T  T  F  N  D  I  I  S  A  V  Q  T  Y  G  D  G  Y  L  S  I  V
         2090              2110              2130              2150
cttagattctcaggtgtaaagaaaaaaatggaactaactcagttctaqGAGAAATATACTCCCTCAGACGGCTCTCTTACCGAACAATTC
                                                 E  K  Y  T  P  S  D  G  S  L  T  E  Q  F
    2170              2190              2210              2230              2250
TCCCGTACAGACGGCACTCCGCTTTCTGCCTCTGCCCTGACTTGGTCGTACGCTTCTCTCCTAACCGCTTCGGCCCGCAGACAGTCCGTC
 S  R  T  D  G  T  P  L  S  A  S  A  L  T  W  S  Y  A  S  L  L  T  A  S  A  R  R  Q  S  V
         2270              2290              2310              2330
GTCCCTGCTTCCTGGGGCGAAAGCTCCGCAAGCAGCGTCCCTGCCGTCTGCTCTGCCACCTCTGCCACGGGCCCATACAGCACGGCTACC
 V  P  A  S  W  G  E  S  S  A  S  S  V  P  A  V  C  S  A  T  S  A  T  G  P  Y  S  T  A  T
    2350              2370              2390              2410              2430
AACACCGTCTGGCCAAGCTCTGGCTCTGGCAGCTCAACAACCACCAGTAGCGCCCCCATGCACCACTCCTACCTCTGTGGCTGTGACCTTC
 N  T  V  W  P  S  S  G  S  G  S  S  T  T  T  S  S  A  P  C  T  T  P  T  S  V  A  V  T  F
         2450              2470              2490              2510
GACGAAATCGTCAGCACCAGTTACGGGGAGACAATCTACCTGGCCGGCTCGATCCCCGAGCTGGGCAACTGGTCCACGGCCAGCGCGATC
 D  E  I  V  S  T  S  Y  G  E  T  I  Y  L  A  G  S  I  P  E  L  G  N  W  S  T  A  S  A  I
    2530              2550              2570              2590              2610
CCCCTCCGCGCGGATGCTTACACCAACAGCAACCCGCTCTGGTACGTGACCGTCAATCTGCCCCCTGGCACCAGCTTCGAGTACAAGTTC
 P  L  R  A  D  A  Y  T  N  S  N  P  L  W  Y  V  T  V  N  L  P  P  G  T  S  F  E  Y  K  F
         2630              2650              2670              2690
TTCAAGAACCAGACGGACGGGACCATCGTCTGGGAAGACGACCCGAACCGGTCGTACACGGTCCCAGCGTACTGTGGGCAGACTACCGCC
 F  K  N  Q  T  D  G  T  I  V  W  E  D  D  P  N  R  S  Y  T  V  P  A  Y  C  G  Q  T  T  A
    2710              2730
ATTCTTGACGATAGTTGGCAGTGAGATAACATCCACCCTTCTGTTTTA
 I  L  D  D  S  W  Q  *
```

FIG 5B

```
1                                                              60
An_amg-1.PRO  M.SF.RSLLALSGLVCTGLA.NVISKRAT..LDSWLSNEATVARTAILNNIGADGAWVSG
Ao_AMG.PRO    MVSF.SSCLRALALGSSVLAVQPVLRQATG.LDTWLSTEANFSRQAILNNIGADGQSAQG
Tal-AMG.PRO   MASLVAGALCILGLTPAAFARAPVAARATGSLDSFLATETPIALQGVLNNIGPNGADVAG
              * *     *      *    *     **  **  *      ***** *      *

61                                                             120
An_amg-1.PRO  ADSGIVVASPSTDNPDYFYTWTRDSGLVLKTLVDLFRNGDTSLLSTIENYISAQAIVQGI
Ao_AMG.PRO    ASPGVVIASPSKSDPDYFYTWTRDSGLVMKTLVDLFRGGDADLLPIIEEFISSQARIQGI
Tal-AMG.PRO   ASAGIVVASPSRSDPNYFYSWTRDAALTAKYLVDAFIAGNKDLEQTIQQYISAQAKVQTI
              *  * ****  * *** *** ****    *  **** *   *    *   **** *  *

121                                                            180
An_amg-1.PRO  SNPSGDLSSGAGLGEPKFNVDETAYTGSVGRPQRDGPALRATAMIGFGQWLLDNGYTSTA
Ao_AMG.PRO    SNPSGALSSG.GLGEPKFNVDETAFTGAWGRPQRDGPALRATAMISFGEWLVENSHTSIA
Tal-AMG.PRO   SNPSGDLSTG.GLGEPKFNVNETAFTGPWGRPQRDGPALRATALIAYANYLIDNGEASTA
              *****  ** * ********* *** **  **************  *   *    * **

181                                                            240
An_amg-1.PRO  TDIVWPLVRNDLSYVAQYWNQTGYDLWEEVNGSSFFTIAVQHRALVEGSAFATAVGSSCS
Ao_AMG.PRO    TDLVWPVVRNDLSYVAQYWSQSGFDLWEEVQGTSFFTVAVSHRALVEGSSFAKTVGSSCP
Tal-AMG.PRO   DEIIWPIVQNDLSYITQYWNSSTFDLWEEVEGSSFFTTAVQHRALVEGNALATRLNHTCS
               * *** * *****  *** *  ******  ***** **  ******      *    *

241                                                            300
An_amg-1.PRO  WCDSQAPEILCYLQSFWTGSFILANFDS.SRSGKDANTLLGSIHTFDPEAACDDSTFQPC
Ao_AMG.PRO    YCDSQAPQVRCYLQSFWTGSYIQANFGG.GRSGKDINTVLGSIHTFDPQATCDDATFQPC
Tal-AMG.PRO   NCVSQAPQVLCFLQSYWTGSYVLANFGGSGRSGKDVNSILGSIHTFDPAGGCDDSTFQPC
               * ****   ** *** ****   ***    ******   ********    ***  *****

301                                                            360
An_amg-1.PRO  SPRALANHKEVVDSFRSIYTLNDGLSDSEAVAVGRYPEDTYYNGNPWFLCTLAAAEQLYD
Ao_AMG.PRO    SARALANHKVVTDSFRSIYAINSGRAENQAVAVGRYPEDSYYNGNPWFLTTLAAAEQLYD
Tal-AMG.PRO   SARALANHKVVTDSFRSIYAINSGIAEGSAVAVGRYPEDVYQGGNPWYLATAAAAEQLYD
              * *******   *******  *       ********** *   *** *   *******

361                                                            420
An_amg-1.PRO  ALYQWDKQGSLEVTDVSLDFFKALYSDAATGTYSSSSSTYSSIVDAVKTFADGFVSIVET
Ao_AMG.PRO    ALYQWDKIGSLAITDVSLPFFKALYSSAATGTYASSTTVYKDIVSAVKAYADGYVQIVQT
Tal-AMG.PRO   AIYQWKKIGSISITDVSLPFFQDIYPSAAVGTYNSGSTTFNDIISAVQTYGDGYLSIVEK
              * ***   **   *****  **   *  ** ***  *   *  *  *    ** ***

421                                                            480
An_amg-1.PRO  HAASNGSMSEQYDKSDGEQLSARDLTWSYAALLTANNRRNSVVPASWGETSASSVPGTCA
Ao_AMG.PRO    YAASTGSMAEQYTKTDGSQTSARDLTWSYAALLTANNRRNAVVPAPWGETAATSIPSACS
Tal-AMG.PRO   YTPSDGSLTEQFSRTDGTPLSASALTWSYASLLTASARRQSVVPASWGESSASSVPAVCS
              *  * **   *    **    **  ******* ****  **  **** *** **   *
```

FIG 6A

```
            481                                                        540
An_amg-1.PRO ATSAIGTYSSVTVTSWPSIVATGGTTTTATPTGSGSVTSTSKTTATASKTSTSTSSTSCT
Ao_AMG.PRO   TTSASGTYSSVVITSWPTISGYPGA....................PDSPCQ
Tal-AMG.PRO  ATSATGPYSTATNTVWPS.............SGSGS..............STTTSSAPCT
             *** * **      * **                                         *

541                                                        600
An_amg-1.PRO TPTAVAVTFDLTATTTYGENIYLVGSISQLGDWETSDGIALSADKYTSSDPLWYVTVTLP
Ao_AMG.PRO   VPTTVSVTFAVKATTVYGESIKIVGSISQLGSWNPSSATALNADSYTTDNPLWTGTINLP
Tal-AMG.PRO  TPTSVAVTFDEIVSTSYGETIYLAGSIPELGNWSTASAIPLRADAYTNSNPLWYVTVNLP
             ** * ***        * *** *   *** ** *      *  * **  *** *  **

601                                   646
An_amg-1.PRO AGESFEYKFIRIESDDSVEWESDPNREYTYPQACGTSTATVTDTWR
Ao_AMG.PRO   AGQSFEYKFIRVQ.NGAVTWESDPNRKYTVPSTCGVKSAVQSDVWR
Tal-AMG.PRO  PGTSFEYKFFKNQTDGTIVWEDDPNRSYTVPAYCGQTTAILDDSWQ
               * ******      ** **** ****  **     *   * *
```

FIG 6B

THERMOSTABLE GLUCOAMYLASE

CROSS-REFERENCE TO RELATED APPLICATIONS

This application is a division of application Ser. No. 09/821,616, filed Mar. 29, 2001, now U.S. Pat. No. 6,620,924, which is a continuation of application Ser. No. 09/199,290 filed Nov. 24, 1998, now U.S. Pat. No. 6,255,084, which is a continuation-in-part of application Ser. Nos. 08/979,673 and 09/107,657 filed Nov. 26, 1997 and Jun. 30, 1998, respectively, and each now abandoned, and claims priority under 35 U.S.C. 1 19 of Danish application nos. 1557/97 and PA 1998 00925 filed Dec. 30, 1997 and Jul. 10, 1998, respectively, and U.S. application Nos. 60/070,746 and 60/094,344 filed Jan. 8, 1998 and Jul. 28, 1998, respectively, the contents of which are fully incorporated herein by reference.

FIELD OF THE INVENTION

The present invention relates to a thermostable glucoamylase suitable for, e.g., starch conversion, e.g., for producing glucose from starch. The present invention also relates to the use of said thermostable glucoamylase in various processes, in particular in the saccharification step in starch convention processes.

BACKGROUND OF THE INVENTION

Glucoamylases (1,4-α-D-glucan glucohydrolase, EC 3.2.1.3) are enzymes which catalyze the release of D-glucose from the non-reducing ends of starch or related oligo and polysaccharide molecules.

Glucoamylases are produced by several filamentous fungi and yeasts, including *Aspergillus niger* and *Aspergillus awamori*.

Commercially, the glucoamylases are used to convert corn starch which is already partially hydrolyzed by an α-amylase to glucose. The glucose may further be converted by glucose isomerase to a mixture composed almost equally of glucose and fructose. This mixture, or the mixture further enriched with fructose, is the commonly used high fructose corn syrup commercialized throughout the world. This syrup is the world's largest tonnage product produced by an enzymatic process. The three enzymes involved in the conversion of starch to fructose are among the most important industrial enzymes produced.

One of the main problems existing with regard to the commercial use of glucoamylase in the production of high fructose corn syrup is the relatively low thermal stability of glucoamylases, such as the commercially available *Aspergillus niger* glucoamylase (i.e., (sold as AMG by Novo Nordisk A/S). The commercial *Aspergillus* glucoamylase is not as thermally stable as α-amylase or glucose isomerase and it is most active and stable at lower pH's than either α-amylase or glucose isomerase. Accordingly, it must be used in a separate vessel at a lower temperature and pH.

U.S. Pat. No. 4,247,637 describes a thermostable glucoamylase having a molecular weight of about 31,000 Da derived from *Talaromyces duponti* suitable for saccharifying a liquefied starch solution to a syrup. The glucoamylase is stated to retain at least about 90% of its initial glucoamylase activity when held at 70° C. for 10 minutes at pH 4.5.

U.S. Pat. No. 4,587,215 discloses a thermostable amyloglucosidase derived from the species *Talaromyces thertnophilus* with a molecular weight of about 45,000 Da. The disclosed amyloglucosidase (or glucoamylase) loses its enzymatic activity in two distinct phases, an initial period of rapid decay followed by a period of slow decay. At 70° C. (pH=5.0) the half-life for the fast decay is about 18 minutes with no measurable loss of activity within an hour in the second phase of decay.

Bunni L et al., (1989), Enzyme Microb. Technol., Vol. 11, p. 370–375, concerns production, isolation and partial characterization of an extracellular amylolytic system composed of at least one form of α-amylase and one form of an α-glucosidase produced by *Talaromyces emersonii* CBS 814.70. Only the α-amylase is isolated, purified and characterized.

BRIEF DISCLOSURE OF THE INVENTION

The present invention is based upon the finding of a novel thermostable glucoamylase suitable for use, e.g., in the saccharification step in starch conversion processes.

The terms "glucoamylase" and "AMG" are used interchangeably below.

The thermal stability of the glucoamylase of the invention is measured as $T_{1/2}$ (half-life) using the method described in the "Materials and Methods" section below.

The inventors of the present invention have isolated, purified and characterized a thermostable glucoamylase from a strain of *Talaromyces emersonii* now deposited with the Centraalbureau voor Schimmelcultures under the number CBS 793.97.

When applied to a protein, the term "isolated" indicates that the protein is found in a condition other than its native environment. In a preferred form, the isolated protein is substantially free of other proteins, particularly other homologous proteins (i.e., "homologous impurities" (see below)).

It is preferred to provide the protein in a greater than 40% pure form, more preferably greater than 60% pure form. Even more preferably it is preferred to provide the protein in a highly purified form, i.e., greater than 80% pure, more preferably greater than 95% pure, and even more preferably greater than 99% pure, as determined by SDS-PAGE.

The term "isolated enzyme" may alternatively be termed "purified enzyme".

The term "homologous impurities" means any impurity (e.g. another polypeptide than the polypeptide of the invention) which originates from the homologous cell, from where the polypeptide of the invention is originally obtained.

The isolated glucoamylase has a very high thermal stability in comparison to prior art glucoamylases, such as the *Aspergillus niger* glucoamylase (available from Novo Nordisk ANS under the trade name AMG). The T½ (half-life) was determined to be about 120 minutes at 70° C. (pH 4.5) as described in Example 2 below. The T½ of the recombinant *T. emersonii* AMG expressed in yeast was determined to be about 110 minutes as described in Example 12.

Therefore, in the first aspect the present invention relates to an isolated enzyme with glucoamylase activity having a $T_{1/2}$ (half-life) of at least 100 minutes in 50 mM NaOAc, 0.2 AGU/ml, pH 4.5, at 70° C.

In the second aspect the invention relates to an enzyme with glucoamylase activity comprising one or more of the partial sequences shown in SEQ ID Nos. 1–6 or the full length enzyme shown in SEQ ID NO: 7 or an enzyme with glucoamylase activity being substantially homologous thereto.

The term "partial sequence" denotes a partial polypeptide sequence which is comprised in a longer polypeptide sequence, wherein said longer polypeptide sequence is having the activity of interest.

The invention also relates to the cloned DNA sequence encoding the glucoamylase of the invention.

Further, the invention also relates to a process of converting starch or partially hydrolyzed starch into a syrup containing, e.g., dextrose, said process including the step of saccharifying starch hydrolyzate in the presence of a glucoamylase of the invention.

It is an object of the invention to provide a method of saccharifying a liquefied starch solution, wherein an enzymatic saccharification is carried out using a glucoamylase of the invention.

Furthermore, the invention relates to the use of a glucoamylase of the invention in a starch conversion process, such as a continuous starch conversion process. In an embodiment of the continuous starch conversion process it includes a continuous saccharification step.

The glucoamylase of the invention may also be used in processes for producing oligosaccharides or specialty syrups.

Finally, the invention relates to an isolated pure culture of the microorganism *Talaromyces emersonii* CBS 793.97 or a mutant thereof capable of producing a glucoamylase of the invention.

BRIEF DESCRIPTION OF THE DRAWINGS

FIG. 5 shows the sequence of the *Talaromyces emersonii* AMG locus. The predicted amino acid sequence is shown below the nucleotide sequence. The four introns are shown in lower case letters. Consensus introns sequences are underlined. Putative signal and pro-peptides are double underlined and dotted underline, respectively;

FIG. 6 shows an alignment/comparison of the amino acid sequences of the *A. niger* AMG (An_amg-1.pro), *A. oryzae* AMG Ao_AMG.pro), and *Talaromyces emersonii* AMG (Tal-AMG.pro). Identical amino acid residues are indicated by a *.
Signal and pro peptides are underlined by a single and a double lined, respectively;

DETAILED DISCLOSURE OF THE INVENTION

Figure 1:
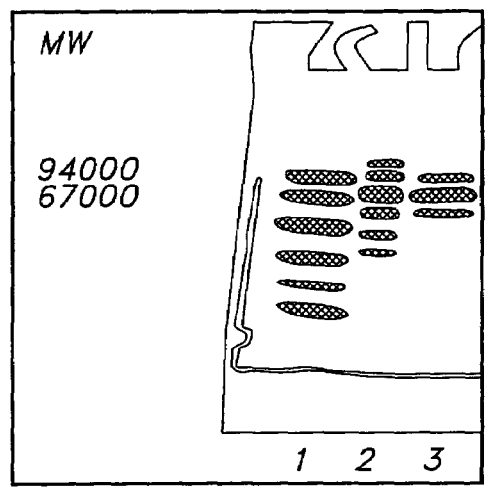
FIG. 1 shows the SDS-PAGE gel (stained with Coomassie Blue) used for determining the molecular weight ($M_w$) of the purified *Talaromyces emersonii* CBS 793.97 glucoamylase of the present invention.
1: Standard marker,
2: Q Sepharose pool (1. run)
3: S Sepharose pool.

The present invention is based upon the finding of a novel thermostable glucoamylase suitable for use in, e.g., the saccharification step in a starch conversion process.

The inventors of the present invention have isolated, purified and characterized a glucoamylase from a strain of *Talaromyces emersonii* CBS 793.97. The glucoamylase turned out to have a very high thermal stability in comparison to prior art glucoamylases.

Accordingly, in a first aspect the present invention relates to an isolated enzyme with glucoamylase activity having a $T_{1/2}$ (half-life) of at least 100 minutes, such as between 100 and 140 minutes, in 50 mM NaOAc, 0.2 AGU/ml, pH 4.5, at 70° C.

T½ (half-life) of the isolated *Talaromyces emersonii* CBS 793.97 glucoamylase was determined to be about 120 minutes at 70° C. as described in Example 2 below and to be about 110° C. for the *T. emersonii* produced in yeast as described in Example 12.

The molecular weight of the isolated glucoamylase was found to be about 70 kDa determined by SDS-PAGE. Further, the pI of said enzyme was determined to be below 3.5 using isoelectrical focusing.

The isoelectric point, pI, is defined as the pH value where the enzyme molecule complex (with optionally attached metal or other ions) is neutral, i.e., the sum of electrostatic charges (net electrostatic charge, NEC) on the complex is equal to zero. In this sum of course consideration of the positive or negative nature of the electrostatic charge must be taken into account.

It is expected that substantially homologous enzymes having the same advantageous properties are obtainable from other micro-organisms, especially fungal organisms such as filamentous fungi, in particular from another strain of *Talaromyces*, especially another strains of *Talaromyces emersonii*.

The Deposited Micro-Organism

An isolate of the filamentous fungus strain, from which the glucoamylase of the invention has been isolated, has been deposited with the Centraalbureau voor Schimmelcultures, P.O. Box 273, 3740 AG Baarn, the Netherlands, for the purposes of patent procedure on the date indicated below. CBS being an international depository under the Budapest Treaty affords permanence of the deposit in accordance with rule 9 of said treaty.
Deposit date: Jun. 2, 1997
Depositor's ref: NN049253
CBS designation: CBS 793.97

The isolate of the filamentous fungus *Talaromyces emersonii* CBS No. 793.97 has been deposited under conditions that assure that access to the isolated fungus will be available during the pendency of this patent application to one determined by the commissioner of Patents and Trademarks to be entitled thereto under 37 C.F.R. § 1.14 and 35 U.S.C § 122. The deposit represents a substantially pure culture of the isolated fungus. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

*Talaromyces emersonii* Glucoamylase Amino Acid Sequence

The inventors have sequenced the thermostable glucoamylase derived from *Talaromyces emersonii* CBS 793.97 as will be described further in the Example 3 below. According to the invention the *Talaromyces* AMG may have a Asp145Asn (or D145N) substitution (using SEQ ID NO: 7 numbering).

Therefore, the invention also relates to an isolated enzyme with glucoamylase activity comprising one or more of the partial sequences shown in SEQ ID NOS: 1–6 or the full length sequence shown in SEQ ID NO: 7 or an enzyme with glucoamylase activity being substantially homologous thereto. SEQ ID NO: 34 shows the full length sequence including the signal and pre propeptide from amino acid no. 1 to 27.

Homology of the Protein Sequence

The homology between two glucoamylases is determined as the degree of identity between the two protein sequences indicating a derivation of the first sequence from the second. The homology may suitably be determined by means of computer programs known in the art such as gap provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, p. 443–453). Using gap with the following settings for polypeptide sequence comparison: gap creation penalty of 3.0 and gap extension penalty of 0.1.

According to the invention a "substantially homologous" amino acid sequence exhibits a degree of identity preferably of at least 80%, at least 90%, more preferably at least 95%, more preferably at least 97%, and most preferably at least 99% with the partial amino acid sequences shown in SEQ ID NO: 1–6 or SEQ ID NO: 7.

The Cloned *Talaromyces emersonii* DNA Sequence

The invention also relates to a cloned DNA sequence encoding an enzyme exhibiting glucoamylase activity of the invention, which DNA sequence comprises:

(a) the glucoamylase encoding part of the DNA sequence shown in SEQ ID NO: 33;
(b) the DNA sequence shown in positions 649–2724 in SEQ ID NO:33 or its complementary strand;
(c) an analogue of the DNA sequence defined in (a) or (b) which is at least 80% homologous with said DNA sequence;
(d) a DNA sequence which hybridizes with a double-stranded DNA probe comprising the sequence shown in 649–2724 in SEQ ID NO: 33 at low stringency;
(e) a DNA sequence which, because of the degeneracy of the genetic code, does not hybridize with the sequences of (b) or (f), but which codes for a polypeptide having exactly the same amino acid sequence as the polypeptide encoded by any of these DNA sequences; or
(g) a DNA sequence which is a fragment of the DNA sequences specified in (a), (b), (c), (d), or (e).

The mature part of the AMG of the invention is encoded by the DNA sequence in position 728–2724 of SEQ ID NO: 33. When expressing the AMG of the invention in yeast, e.g., *Saccharomyces cerevisiae* YNG318, the introns need to be cut out as described in Example 7.

Homology of DNA Sequences

The DNA sequence homology referred to above is determined as the degree of identity between two sequences indicating a derivation of the first sequence from the second. The homology may suitably be determined by means of computer programs known in the art, such as GAP provided in the GCG program package (Program Manual for the Wisconsin Package, Version 8, August 1994, Genetics Computer Group, 575 Science Drive, Madison, Wis., USA 53711)(Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the coding region of the analogous DNA sequences referred to above exhibits a degree of identity preferably of at least 80%, more preferably at least 90%, more preferably at least 95%, more preferably at least 97% with the AMG encoding part of the DNA sequence shown in SEQ ID NO: 33 or the glucoamylase encoding part with or witout introns.

Hybridization:

The hybridization conditions referred to above to define an analogous DNA sequence as defined in d) above which hybridizes to a double-stranded DNA probe comprising the sequence shown in positions 649–2748 in SEQ ID NO: 33 (i.e., the AMG encoding part), under at least low stringency conditions, but preferably at medium or high stringency conditions are as described in detail below.

Suitable experimental conditions for determining hybridization at low, medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5× Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6–13), $^{32}$P-dCTP-labeled (specific activity>1×10$^9$ cpm/µg) probe for 12 hours at about 45° C. The filter is then washed twice for 30 minutes in 2×SSC, 0.5% SDS at about 55° C. (low stringency), more preferably at about 60° C. (medium stringency), still more preferably at about 65° C. (medium/high stringency), even more preferably at about 70° C. (high stringency), and even more preferably at about 75° C. (very high stringency).

Molecules to which the oligonucleotide probe hybridizes under these conditions are detected using a x-ray film.

Starch Conversion

The present invention provides a method of using the thermostable glucoamylase of the invention for producing glucose and the like from starch. Generally, the method includes the steps of partially hydrolyzing precursor starch in the presence of α-amylase and then further hydrolyzing the release of D-glucose from the non-reducing ends of the starch or related oligo and polysaccharide molecules in the presence of glucoamylase by cleaving α-(1→4) and α-(1→6) glucosidic bonds.

The partial hydrolysis of the precursor starch utilizing α-amylase provides an initial breakdown of the starch molecules by hydrolyzing internal α-(1→4)-linkages. In commercial applications, the initial hydrolysis using α-amylase is run at a temperature of approximately 105° C. A very high starch concentration is processed, usually 30% to 40% solids. The initial hydrolysis is usually carried out for five minutes at this elevated temperature. The partially hydrolyzed starch can then be transferred to a second tank and incubated for approximately one hour at a temperature of 85° to 90° C. to derive a dextrose equivalent (D.E.) of 10 to 15.

The step of further hydrolyzing the release of D-glucose from the non-reducing ends of the starch or related oligo and polysaccharides molecules in the presence of glucoamylase is normally carried out in a separate tank at a reduced temperature between 30° and 60° C. Preferably the temperature of the substrate liquid is dropped to between 55° and 60° C. The pH of the solution is dropped from 6 to 6.5 to a range between 3 and 5.5. Preferably, the pH of the solution is 4 to 4.5. The glucoamylase is added to the solution and the reaction is carried out for 24–72 hours, preferably 36–48 hours.

By using a thermostable glucoamylase of the invention saccharification processes may be carried out at a higher temperature than traditional batch saccharification processes. According to the invention saccharification may be carried out at temperatures in the range from above 60–80° C., preferably 63–75° C. This applies both for traditional batch processes (described above) and for continuous saccharification processes.

Actually, continuous saccharification processes including one or more membrane separation steps, i.e., filtration steps, must be carried out at temperatures of above 60° C. to be able to maintain a reasonably high flux over the membrane. Therefore, a thermostable glucoamylase of the invention provides the possibility of carrying out large scale continuous saccharification processes at a fair price within and period of time acceptable for industrial saccharification processes. According to the invention the saccharification time may even be shortened.

The activity of a glucoamylase of the invention is generally substantially higher at temperatures between 60° C.–80° C. than at the traditionally used temperature between 30–60° C. Therefore, by increasing the temperature at which the glucoamylase operates the saccharification process may be carried out within a shorter period of time or the process may be carried out using lower enzyme dosage.

As the thermal stability of the glucoamylase of the invention is very high in comparison to, e.g., the commercially available Aspergillus niger glucoamylase (i.e., AMG) a less amount of glucoamylase needs to be added to replace the glucoamylase being inactivated during the saccharification process. More glucoamylase is maintained active during saccharification process according to the present invention. Furthermore, the risk of microbial contamination is also reduced when carrying the saccharification process at temperature above 63° C.

By using a glucoamylase with increased specific activity (measured as activity towards maltose), a lower enzyme dosage may be required in the saccharification process.

Examples of saccharification processes, wherein the glucoamylase of the invention may advantageously be used include the processes described in JP 3-224493; JP 1-191693; JP 62-272987; and EP 452,238.

In a further aspect the invention relates to a method of saccharifying a liquefied starch solution, which method comprises an enzymatic saccharification step using a glucoamylase of the invention.

The glucoamylase of the invention may be used in the present inventive process in combination with an enzyme that hydrolyzes only α-(1→6)-glucosidic bonds in molecules with at least four glucosyl residues. Preferably, the glucoamylase of the invention is used in combination with pullulanase or isoamylase. The use of isoamylase and pullulanase for debranching, the molecular properties of the enzymes, and the potential use of the enzymes with glucoamylase is set forth in G.M.A. van Beynum et al., Starch Conversion Technology, Marcel Dekker, New York, 1985, 101–142.

In a further aspect the invention relates to the use of a glucoamylase of the invention in a starch conversion process.

Further, the glucoamylase of the invention may be used in a continuous starch conversion process including a continuous saccharification step.

The glucoamylase of the invention may also be used in immobilised form. This is suitable and often used for producing speciality syrups, such as maltose syrups, and further for the raffinate stream of oligosaccharides in connection with the production of fructose syrups.

The glucoamylase of the invention may also be used in a process for producing ethanol for fuel or beverage or may be used in a fermentation process for producing organic compounds, such as citric acid, ascorbic acid, lysine, glutamic acid.

Materials and Methods

Material

Enzymes:

Glucoamylase derived from the deposited filamentous fungus *Talaromyces emersonii* CBS No. 793.97 has been deposited with the Centraalbureau voor Schimmelcultures, P.O. Box 273, 3740 AG Baarn, the Netherlands, for the purposes of patent procedure on the date indicated below. CBS being an international depository under the Budapest Treaty affords permanence of the deposit in accordance with rule 9 of said treaty.

Deposit date: Jun. 2, 1997

Depositors ref.: NN049253

CBS designation: CBS 793.97

Glucoamylase G1 derived from *Aspergillus niger* disclosed in Boel et al. (1984), EMBO J. 3 (5), 1097–1102, available from Novo Nordisk and shown in SEQ ID NO: 9.

Strains:

JaL228; Construction of this strain is described in WO98/12300

SMO110; Construction of this strain is described in Example 6

Yeast Strain: *Saccharomyces cerevisiae* YNG318: MATa leu2-D2 ura3-52 his4-539 pep4-D1[cir+].

Genes:

*A. niger* G1 glucoamylase gene is shown in SEQ ID NO: 8

*T. emersonii* glucoamylase gene with introns is shown in FIG. 5 and SEQ ID NO: 33. The introns are shown in FIG. 5.

Plasmids:

pJSO026 (*S. cerevisiae* expression plasmid)(J. S. Okkels, (1996)" A URA3-promoter deletion in a pYES vector increases the expression level of a fungal lipase in *Saccharomyces cerevisiae*. Recombinant DNA Biotechnology III: The Integration of Biological and Engineering Sciences, vol. 782 of the Annals of the New York Academy of Sciences) More specifically, the expression plasmid pJSO26, is derived from pYES 2.0 by replacing the inducible GAL1-promoter of pYES 2.0 with the constitutively expressed TPI (triose phosphate isomerase)-promoter from *Saccharomyces cerevisiae* (Albert and Karwasaki, (1982), J. Mol. Appl Genet., 1, 419–434), and deleting a part of the URA3 promoter.

pJaL497; Construction of this plasmid is described in Example 5 pJaL507; Construction of this plasmid is described in Example 5 pJaL510; Construction of this plasmid is described in Example 5 pJaL511; Construction of this plasmid is described in Example 5 pJaL518; Construction of this plasmid is described in Example 6 pCaHj483; Construction of this plasmid is described in Example 6 pJRoy10; Construction of this plasmid is described in Example 6 pJRoy17; Construction of this plasmid is described in Example 6 pSMO127; Construction of this plasmid is described in Example 6 pCR™II; Available from Invitrogen Corporation, San Diego, Calif., USA.

Equipment:

Automatic DNA Sequencer (Applied Biosystems Model 377)

| Media: | |
|---|---|
| SC-ura medium: | |
| Yeast Nitrogen w/o ami | 7.5 g |
| Bernsteinsaüre (Ravsyre) | 11.3 g |
| NaOH | 6.8 g |
| Casaminoacid w/o vit | 5.6 g |
| Tryptophan | 0.1 g |
| Dest. water ad | 1000 ml |

Autoclaved for 20 minutes at 121° C.

From a sterile stock solution of 5% Threonin 4 ml is added to a volume of 900 ml together with 100 ml of a sterile 20% glucose.

| YPD medium: | |
|---|---|
| Yeast extract | 10 g |
| Peptone | 20 g |
| Dest. water ad | 1000 ml |

Autoclaved for 20 minutes at 121° C.
100 ml of a sterile 20% glucose is added to 900 ml.

Methods:

Determination of AGU Activity

One Novo Amyloglucosidase Unit (AGU) is defined as the amount of enzyme which hydrolyzes 1 micromole maltose per minute under the following standard conditions:
Substrate . . . maltose
Temperature . . . 25° C.
pH . . . 4.3 (acetate buffer)
Reaction time . . . 30 minutes A detailed description of the analytical method (AF22) is available on request.

Determination of PUN Activity

PUN is defined as the amount of enzyme which hydrolyzes pullulan (0.2% pullulan, 40° C., pH 5.0), liberating reducing carbohydrate with a reducing power equivalent to 1 micro-mol glucose pr. minute.

Determination of AFAU Activity

The activity is determined in AFAU calculated as the reduction in starch concentration at pH 2.5, 40° C., 0.17 g/l starch and determined by an iodine-starch reaction.

Thermal Stability I (T½ (Half-Life) Determination of AMG

The thermal stability of glucoamylase (determined as T½ (half-life)) is tested using the following method: 950 microliter 50 mM sodium acetate buffer (pH 4.5) (NaOAc) is incubated for 5 minutes at 70° C. 50 microliter enzyme in buffer (4 AGU/ml) is added. 2×40 microliter samples are taken at fixed periods between 0 and 360 minutes and chilled on ice. After chilling the samples the residual enzyme activity is measured using the AGU determination assay (described above). The activity (AGU/ml) measured before incubation (0 minutes) is used as reference (100%). $T_{1/2}$ is the period of time until which the percent relative activity is decreased to 50%.

Determination of Thermal Stability II 1600 microliter of a supernatant and 400 microliter of 0.5 M NaAC pH 4.5 is mixed.

7 eppendorph tubes each containing 250 microliter of the mixture are incubated in a Perkin Elmer thermocycler at 68° C. or 70° C. for 0, 5, 10, 20, 30, 45 and 60 minutes.

100 microliter from each mixture is mixed with 100 microliter of 5 mM CNPG3 (2-chloro-4-Nitrophenyl-Alpha-Maltotrioside from genzyme) in microtiterwells. After incubation for 30 minutes at 37° C. the absorbance is measured at 405 nm.

Determination of Specific Activity of a Glucoamylase 750 microL substrate is incubated 5 minutes at selected temperatures, such as 37° C., 60° C. or 70° C.

50 microL enzyme diluted in sodium acetate is added, and the activity was determined using the AGU standard method described above. The kinetic parameters: Kcat and Km are measured at 45° C. by adding 50 microL enzyme diluted in sodium acetate to preheated 750 microL substrate. Aliquots of 100 microL are removed after 0, 3, 6, 9 and 12 minutes and transferred to 100 microL 0.4 M Sodium hydroxide to stop the reaction. A blank is included.

20 microL is transferred to a Micro titre plates and 200 microL GOD-Perid solution is added. Absorbance is measured at 650 nm after 30 minutes incubation at room temperature.

Glucose is used as standard, and the specific activity is calculated as $k_{cat}$ (sec.$^{-1}$)

Transformation of *Aspergillus oryzae* (General Procedure)

100 ml of YPD (Sherman et al., (1981), Methods in Yeast Genetics, Cold Spring Harbor Laboratory) is inoculated with spores of *A. oryzae* and incubated with shaking for about 24 hours. The mycelium is harvested by filtration through miracloth and washed with 200 ml of 0.6 M $MgSO_4$. The mycelium is suspended in 15 ml of 1.2 M $MgSO_4$, 10 mM $NaH_2PO_4$, pH 5.8. The suspension is cooled on ice and 1 ml of buffer containing 120 mg of Novozym™ 234 is added. After 5 min., 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayed with 5 ml of 0.6 M sorbitol, 100 mM Tris-HCl, pH 7.0. Centrifugation is performed for 15 min. at 1000 g and the protoplasts are collected from the top of the $MgSO_4$ cushion. 2 volumes of STC (1.2 M sorbitol, 10 mM Tris-HCl, pH 7.5, 10 mM $CaCl_2$) are added to the protoplast suspension and the mixture is centrifugated for 5 min. at 1000 g. The protoplast pellet is resuspended in 3 ml of STC and repelleted. This is repeated. Finally, the protoplasts are resuspended in 0.2–1 ml of STC.

100 μl of protoplast suspension are mixed with 5–25 μg of p3SR2 (an *A. nidulans* amdS gene carrying plasmid described in Hynes et al., Mol. and Cel. Biol., Vol. 3, No. 8, 1430–1439, August 1983) in 10 μl of STC. The mixture is left at room temperature for 25 min. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution are added and carefully mixed. The mixture is left at room temperature for 25 min., spun at 2.500 g for 15 min. and the pellet is resuspended in 2 ml of 1.2 M sorbitol. After one more sedimentation the protoplasts are spread on minimal plates (Cove, (1966), Biochem. Biophys. Acta 113, 51–56) containing 1.0 M sucrose, pH 7.0, 10 mM acetamide as nitrogen source and 20 mM CsCl to inhibit background growth. After incubation for 4–7 days at 37° C. spores are picked, suspended in sterile water and spread for single colonies. This procedure is repeated and spores of a single colony after the second re-isolation are stored as a defined transformant.

Fed Batch Fermentation

Fed batch fermentation is performed in a medium comprising maltodextrin as a carbon source, urea as a nitrogen source and yeast extract. The fed batch fermentation is performed by inoculating a shake flask culture of fungal host cells in question into a medium comprising 3.5% of the carbon source and 0.5% of the nitrogen source. After 24 hours of cultivation at pH 5.0 and 34° C. the continuous supply of additional carbon and nitrogen sources are initiated. The carbon source is kept as the limiting factor and it is secured that oxygen is present in excess. The fed batch cultivation is continued for 4 days, after which the enzymes can be recovered by centrifugation, ultrafiltration, clear filtration and germ filtration. Further purification may be done by anionexchange chromatographic methods known in the art.

Transformation of *Saccharomyces cerevisiae* YNG318

The DNA fragments and the opened vectors are mixed and transformed into the yeast *Saccharomyces cerevisiae* YNG318 by standard methods.

EXAMPLES

Example 1

Purification 3500 ml *T. emersonii* culture broth from wild-type fermentation with 0.05 AGU/ml was centrifuged at 9000 rpm followed by vacuum filtration through filter paper and finally a blank filtration. The following procedure was then used to purify the enzyme:

Phenyl Sepharose (250 ml): 1.3 M AMS/10 mM Tris/2 mM $CaCl_2$, pH 7; elution with 10 mM Tris/2 mM $CaCl_2$, pH 7.

Dialysis: 20 mM NaAc, 2 mM $CaCl_2$, pH 5.

Q Sepharose (100 ml): 20 mM NaAc, 2 mM $CaCl_2$, pH 5; elution with a linear gradient from 0–0.4 M NaCl over 10 column volumes.

Dialysis: 20 mM NaAc, 2 mM $CaCl_2$, pH 5.

Colour removal: 0.5% coal in 10 minutes.

Q Sepharose (20 ml): 20 mM NaAc, 2 mM $CaCl_2$, pH 4.5; elution with a linear gradient from 0–0.4 M NaCl over 10 column volumes.

Dialysis: 20 mM NaAc, 2 mM $CaCl_2$, pH 5.

S Sepharose (1 ml): 5 mM citric acid, pH 2.9; elution with a linear gradient from 0–0.3 M NaCl over 10 column volume.

A purity of the enzyme of more than 90% was obtained after the S Sepharose step.

Example 2

Characterisation of the *Talaromyces emersonii* Glucoamylase

The purified *Talaromyces emersonii* CBS 793.97 glucoamylase was used for characterisation.

Molecular Weight ($M_w$)

The molecular weight was determined by SDS-PAGE to around 70 kDa as shown in FIG. 1.

pI

The pI was determined to lie below 3.5 by isoelectrical focusing (Amploline PAG, pH 3.5–9.5 from Pharmacia).

pH Profile

The pH-activity dependency of the *Talaromyces emersonii* glucoamylase was determined and compared with profile of *Aspergillus niger* glucoamylase.

Figure 2:
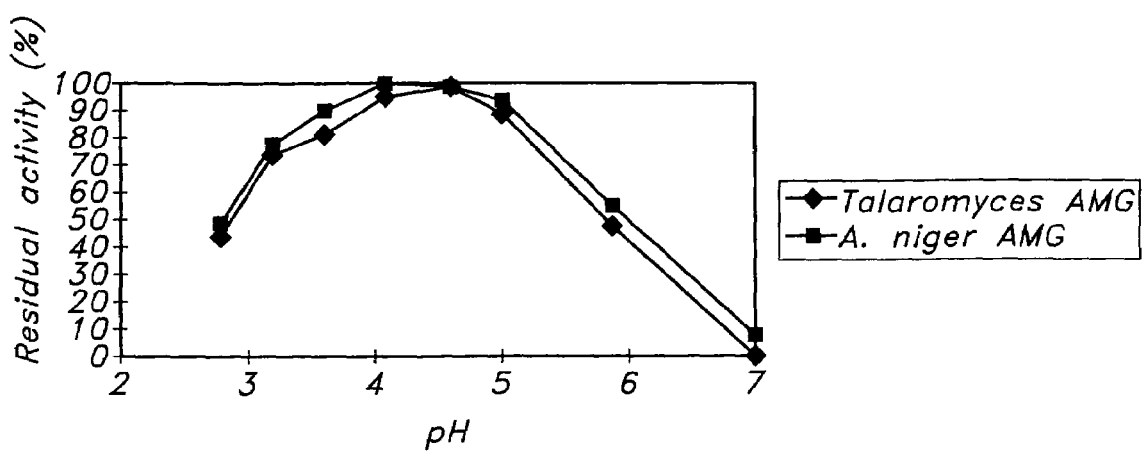
FIG. 2 shows the pH activity profile of *Talaromyces emersonii* and *Aspergillus niger* glucoamylase (AMG) in 0.5% maltose at 60° C.

The pH activity profile was determined using 0.5% maltose as substrate in 0.1 M sodium acetate at 60° C. The pH was measured in duple samples comprising 0.1–1 AGU/ml. The result of the test is shown in FIG. 2.

Temperature Profile

The temperature-activity dependency of the *Talaromyces emersonii* glucoamylase of the invention was determined and compared with the profile of *Aspergillus niger* glucoamylase.

Figure 3:
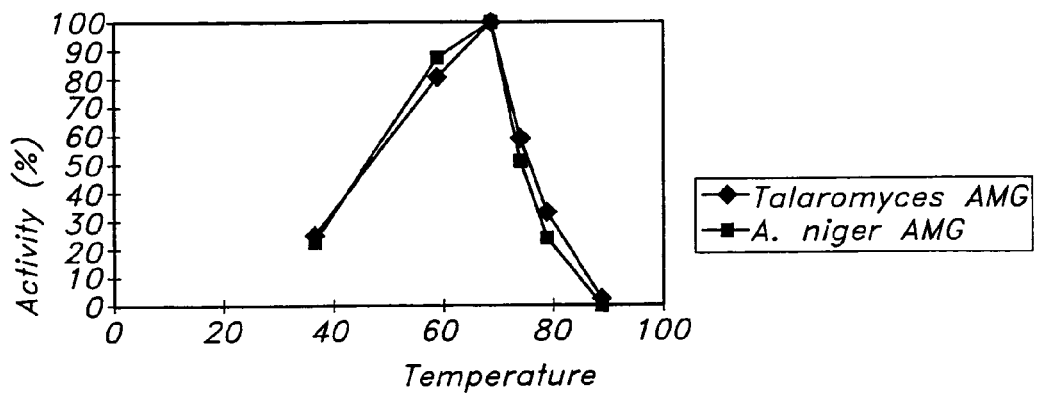
FIG. 3 shows the temperature activity profile of the *Talaromyces emersonii* CBS 793.97 glucoamylase vs. *Aspergillus niger* glucoamylase (AMG)

200 μl 0.5% maltose, pH 4.3 was incubated at 37, 50, 60, 70, 75, 80 and 90° C. and the reaction was started by adding 10 μl enzyme (0.25 AGU/ml); reaction time was 10 minutes. The result of the test is shown in FIG. 3.

Temperature Stability—T½ (Half-Life)

The thermal stability of the *Talaromyces emersonii* glucoamylase was determined and compared with the thermal stability of *Aspergillus niger* glucoamylase.

The method used is described above in the "Material and Methods" section as "Thermal Stability I (T½ (half-life) determination of AMG".

Figure 4:
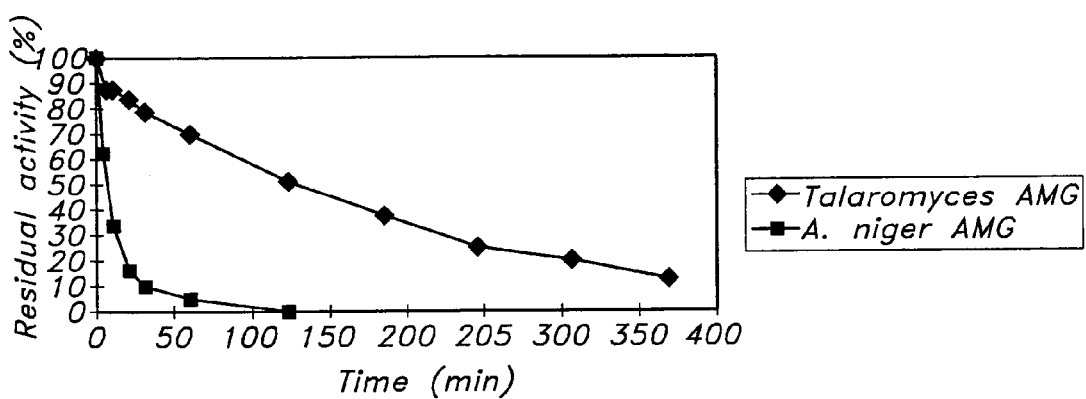
FIG. 4 shows the curve for determining $T_{1/2}$ (half-life) in 50 mM NaOAc, 0.2 AGU/ml, pH 4.5, at 70° C. of *Talaromyces emersonii* CBS 793.97 glucoamylase vs. *Aspergillus niger* glucoamylase (AMG)

The T½ of the *Talaromyces emersonii* glucoamylase was determined to about 120 minutes at 70° C. The T½ of the *Aspergillus niger* glucoamylase was determined to 7 minutes under the same conditions (See FIG. 4).

Specific Activity

The extension coefficient was determined to: ϵ=2.44 ml/mg*cm on basis of absorbency at 280 nm and protein concentration. The specific activity towards maltose at 37° C. was then calculated to 7.3 AGU/mg. Purity of the sample was approximately 90% and a corrected specific activity is therefore 8.0 AGU/mg. Following specific activities were measured:

|  | Specific activity (AGU/mg) | | |
| --- | --- | --- | --- |
| AMG | 37° C. | 60° C. | 70° C. |
| T. emersonii | 8.0 | 21 | 27 |
| A. niger | 2.0 | 6.6 | 8.0 |

*) Estimated for Pure Enzyme.

Example 3

Sequencing of the N-Terminal of T. emersonii Glucoamylase

The N-terminal amino acid sequence of T. emersonii glucoamylase was determined following SDS-PAGE and electroblotting onto a PVDF-membrane. Peptides were derived from reduced and S-carboxymethylated glucoamylase by cleaving with a lysyl-specific protease. The resulting peptides were fractionated and re-purified using RP-HPLC before subjected to N-terminal sequence determination.

```
N-terminal sequence (SEQ ID NO: 1):
Ala Asn Gly Ser Leu Asp Ser Phe Leu Ala Thr Glu
Xaa Pro Ile Ala Leu Gln Gly Val Leu Asn Asn Ile
Gly Peptide 1 (SEQ ID NO: 2):
Val Gln Thr Ile Ser Asn Pro Ser Gly Asp Leu Ser
Thr Gly Gly Leu Gly Glu Pro Lys Peptide 2 (SEQ ID NO: 3):
Xaa Asn Val Asn Glu Thr Ala Phe Thr Gly Pro Xaa
Gly Arg Pro Gln Arg Asp Gly Pro Ala Leu Peptide 3 (SEQ ID NO: 4):
Asp Val Asn Ser Ile Leu Gly Ser Ile His Thr Phe
Asp Pro Ala Gly Gly Cys Asp Asp Ser Thr Phe Gln
Pro Cys Ser Ala Arg Ala Leu Ala Asn His Lys Peptide 4 (SEQ ID NO: 5):
Thr Xaa Ala Ala Ala Glu Gln Leu Tyr Asp Ala Ile
Tyr Gln Trp Lys Peptide 5 (SEQ ID NO: 6):
Ala Gln Thr Asp Gly Thr Ile Val Trp Glu Asp Asp
Pro Asn Arg Ser Tyr Thr Val Pro Ala Tyr Cys Gly
Gln Thr Thr Ala Ile Leu Asp Asp Ser Trp Gln Xaa denoted a residue that could not be assigned.
```

Example 4

The Full Length T. emersonii Glucoamylase

The full length T. emersonii glucoamylase amino acid sequence shown in SEQ ID NO: 7 was identified using standard methods.

Example 5

Cloning and Sequencing of the Talaromyces emersonii Glucoamylase Gene

PCR cloning parts of the Talaromyces emersonii AMG gene

For cloning of the Talaromyces emersonii AMG gene degenerated primers shown in table 1 was designed for PCR amplification of part of the AMG gene.

TABLE 1

| Primer no: | Sequence | Comments |
| --- | --- | --- |
| 102434 | V L N N I G | N-Terminal |
| (SEQ ID NO: 10) | 5'-GTNTTRAAYAAYATHGG | 5' primers |
| 102435 | 5'-GTNCTNAAYAAYATHGG | |
| (SEQ ID NO: 11) | | |
| 117360 | D L W E E V | Active site |
| (SEQ ID NO: 12) | CTRGANACCCTYCTYCA-5' | consensus 3' primers |
| 117361 | CTRAAYACCCTYCTYCA-5' | |
| (SEQ ID NO: 13) | | |
| 127420 | W E D D P N | C-Terminal |
| (SEQ ID NO: 14) | ACCCTYCTRCTGGGNTT-5' | 3' primers |

Genomic DNA from Talaromyces emersonii was prepared from protoplasts made by standard procedures [cf.e.g., Christensen et al. Biotechnology 1989 6 1419–1422] and was used as template in the PCR reaction. Amplification reaction were performed in 100 μl volumes containing 2.5 units Taq-polymerase, 100 ng of A. oryzae genomic DNA, 50 mM KCl, 10 mM Tris-HCl pH 8.0, 1.5 mM MgCl₂, 250 nM of each dNTP, and 100 pM of each of the following primers sets: 102434/117360, 102434/117361, 102435/117360, 102434/117361, 102434/127420, and 102434/127420.

Amplification was carried out in a Perkin-Elmer Cetus DNA Termal 480, and consisted of one cycle of 3 minutes at 94° C., followed by 30 cycles of 1 minutes at 94° C., 30 seconds at 40° C., and 1 minutes at 72° C. Only the PCR reaction 102434/117360 gave products. Four bands was detected with the following sizes 1400, 800, 650, and 525 bp. All four bands were purified and cloned into the vector pCR®2.1 (Invitrogen®). Sequencing of a few clone from each band and sequence comparisons to the A. niger AMG, releaved that a clone from the 650 bp band encodes for the N-terminal part of the Talaromyces emersonii AMG. This clone was designated pJaL497.

To obtained more of the gene a specific primer (123036: 5'-GTGAGCCCAATTCAATGTG-3' (SEQ ID NO:15) was made out from the sequence of clone pJaL497. The primer set 123036/127420 was used for PCR on Talaromyces genomic DNA and a single fragment on 1500 bp was obtained. The PCR fragment was clone into the vector pCR®2.1 and sequenced. By sequencing the clone was confirmed to encoded the C-terminal part of the Talaromyces emersonii AMG. The clone was designated pJaL507.

Genomic Restriction Mapping and Cloning of a Genomic Clone(s)

Taken together the two clones pJaL497 and pJaL507 covered about 95% of the AMG gene. In order to clone the missing part of the AMG gene a genomic restriction map was constructed by using the two PCR fragment as probes to a Southern blot of Talaromyces emersonii genomic DNA digested with single or a combination of a number of restriction enzymes. This shows that the Talaromyces emersonii AMG gene is located on two EcoRI fragment on about 5.6 kb and 6.3 kb, respectively.

Talaromyces emersonii genomic DNA was digested with EcoRI and fragments with the size between 4–7 kb was purified and used for construction of a partially genome library in Lambda ZAP II as described by the manufactory instruction (Stratagene). The library was first screened using the 0.7 kb EcoRI fragment from pJaL497 (encoding the N-terminal half of the AMG gene) as probe to get the start of the AMG gene. One clone was obtained and designated pJaL511. In a second screening of the library using a 0.75 kb EcoRV fragment from pJaL507 (encoding the C-terminal half of the AMG gene) as probe in order to get the C-terminal end of the AMG gene. One clone was obtained and designated pJaL510.

Sequence Analysis of the *Talaromyces emersonii* AMG Gene

The AMG gene sequence was obtained by sequencing on the plasmids: pJaL497, pJaL507, pJaL510, and pJaL511 and on subclones hereof with the standard reverse and forward primers for pUC. Remaining gabs were closed by using specific oligonucleotide as primers.

Potential introns were found by comparing the sequence with consensus sequences for introns in *Aspergillus* and with the *A. niger* AMG sequence. The *Talaromyces emersonii* AMG nucleotide sequence has an open reading frame encoding a protein on 618 amino acid, interrupted by four introns of 57 bp, 55 bp, 48 bp, and 59 bp, respectively. The nucleotide sequence (with introns) and deduced amino acid sequence is shown in FIG. 5. The DNA sequence (with introns) is also shown in SEQ ID NO: 33 and the *Talaromyces emersonii* AMG sequence (with signal sequence from 1 to 27) is shown in SEQ ID NO: 34. Comparison of the deduced amino acid sequence with the *A. oryzae* AMG and *A. niger* AMG shows an identity of 60.1% and 60.5%, respectively. Alignment of the amino acid sequences shown in FIG. 6 shows that the *Talaromyces* AMG has a very short hinge between the catalytic domain and the starch binding domain, which is also seen for the *A. oryzae* AMG.

Example 6

Construction of the *Aspergillus* Vector pCaHj483

Figure 7:
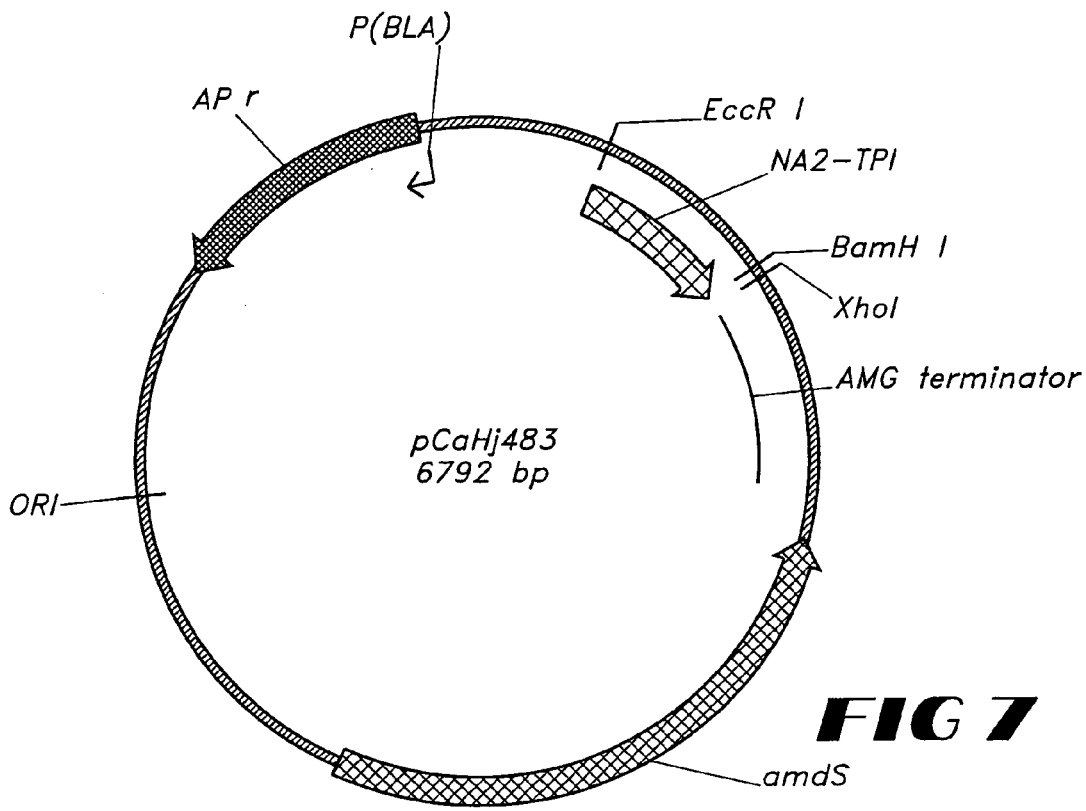
FIG. 7 shows the *Aspergillus* expression cassette pCaHj483 used in Example 5.

Construction of pCaHj483 is depicted in FIG. 7. Said plasmid is build from the following fragments:
a) The vector pToC65 (WO 91/17243) cut with EcoRI and XbaI.
b) A 2.7 kb XbaI fragment from *A. nidulans* carrying the amdS gene (C. M. Corrick et al., Gene 53, (1987), 63–71). The amdS gene is used as a selective marker in fungal transformations. The amdS gene has been modified so that the BamHI site normally present in the gene is destroyed. This has been done by introducing a silent point mutation using the primer: 5'-AGAAATCGGGTATCCTTTCAG-3' (SEQ ID NO:16)
c) A 0.6 kb EcoRI/BamHI fragment carrying the *A. niger* NA2 promoter fused to a 60 bp DNA fragment of the sequence encoding the 5' untranslated end of the mRNA of the *A. nidulans* tpi gene. The NA2 promoter was isolated from the plasmid pNA2 (described in WO 89/01969) and fused to the 60 bp tpi sequence by PCR. The primer encoding the 60 bp tpi sequence had the following sequence:

```
5'-GCTCCTCATGGTGGATCCCCAGTTGTGTAT   (SEQ ID NO: 17)
ATAGAGGATTGAGGAAGGAAGAGAAGTGTGGATA
GAGGTAAATTGAGTTGGAAACTCCAAGCATGGCA
TCCTTGC-3'
``` d) A 675 bp XbaI fragment carrying the *A. niger* glucoamylase transcription terminator. The fragment was isolated from the plasmid pICAMG/Term (described in EP 0238 023).

The BamHI site of fragment c was connected to the XbaI site in front of the transcription terminator on fragment d via the pIC19R linker (BamHI to XbaI)

Construction of a AMG Expression Plasmid, pJaL518

The coding region of the *Talaromyces emersonii* AMG gene was amplified by PCR, using the following two oligonucleotides primers: 139746: 5'-GACAGATCTCCAC-CATGGCGTCCCTCGTTG 3' (SEQ ID NO:18); and primer 139747: 5'-GACCTCGAGTCACTGCCMCTATCGTC 3' (SEQ ID NO:19). The underlined regions indicate sequences present in the *Talaromyces emersonii* AMG gene. To facilitate cloning a restriction enzyme site was inserted into the 5' end of each primer; primer 139746 contains a BglII site and primer 139747 contains a XhoI site.

*Talaromyces emersonii* genomic DNA was used as template in the PCR reaction. The reaction was performed in a volume of 100 µl containing 2.5 units Taq polymerase, 100 ng of pSO2, 250 nM of each dNTP, and 10 pmol of each of the two primers described above in a reaction buffer of 50 mM KCl, 10 mM Tris-HCl pH 8.0, 1.5 mM $MgCl_2$.

Figure 8:
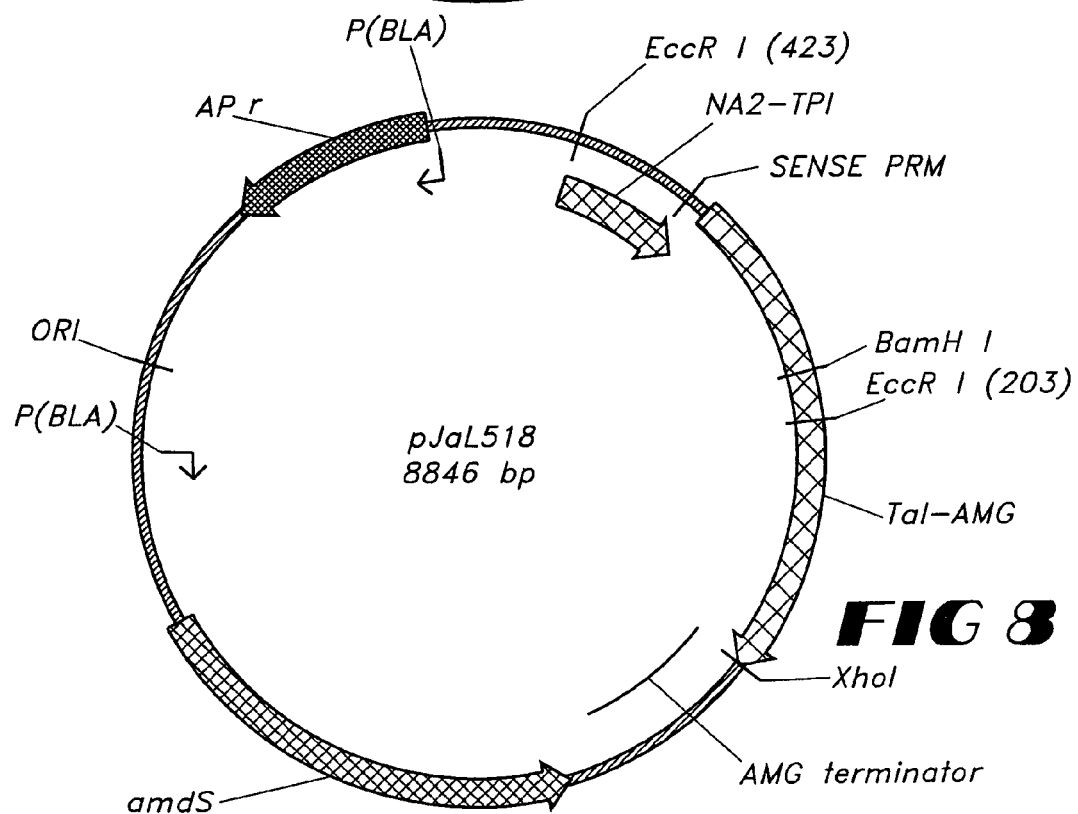
FIG. 8 shows the *Aspergillus* expression plasmid, pJaL518, for the *Talaromyces emersonii* AMG gene.

Amplification was carried out in a Perkin-Elmer Cetus DNA Termal 480, and consisted of one cycle of 3 minutes at 94° C., followed by 25 cycles of 1 minute at 94° C., 30 seconds at 55° C., and 1 minute at 72° C. The PCR reaction produced a single DNA fragment of 2099 bp in length. This fragment was digested with BglII and XhoI and isolated by gel electrophoresis, purified, and cloned into pCaHj483 digested with BamHI and XhoI, resulting in a plasmid which was designated pJaL518. Thus, the construction of the plasmid pJal518 resulted in a fungal expression plasmid for the *Talaromyces emersonii* AMG gene (FIG. 8).

Construction of the *Aspergillus niger* Strain, SMO110

1. Cloning of *A. niger* pyrG Gene

A library of *A. niger* BO-1 was created in EMBL4 as described by the manufactury instructions. The library was screened with a DIG labelled oligonucleotides (PyrG: 5'-CCCTCACCAGGGGAATGCTGCAGTTGATG-3' (SEQ ID NO:20) which was designed from the published *Aspergillus niger* sequence (Wilson et al. Nucleic Acids Res. 16, (1988), 2339–2339). A positive EMBL4 clone which hybridized to the DIG probe was isolated from the BO-1 library, and a 3.9 kb XbaI fragment containing the pyrG gene was subcloned from the EMBL4 clone and clone into pUC118 to create pJRoy10.

2. Cloning of the *A. niger* Glucoamylase (AMG) Gene

The above *A. niger* BO-1 library was screened with a DIG labelled PCR fragment generated by amplification on *A. niger* genomic DNA with the following oligonucleotides, 950847: 5'-CGCCATTCTCGGCGACTT-3' (SEQ ID NO:21), and oligonucleotide 951216: 5'-CGCCGCGGTAT-TCTGCAG-3' (SEQ ID NO:22), which was designed from the published *Aspergillus niger* sequence (Boel et al., EMBO J. 3, (1984), 1581–1585). A positive EMBL4 clone which hybridized to the DIG probe was isolated from the BO-1 library, and a 4.0 kb SpeI fragment containing the AMG gene was subcloned from the EMBL4 clone and clone into pBluescriptSK+ generating plasmid pJRoy17a.

3. Construction of the *A. niger* AMG Disruption Cassette

Figure 9:
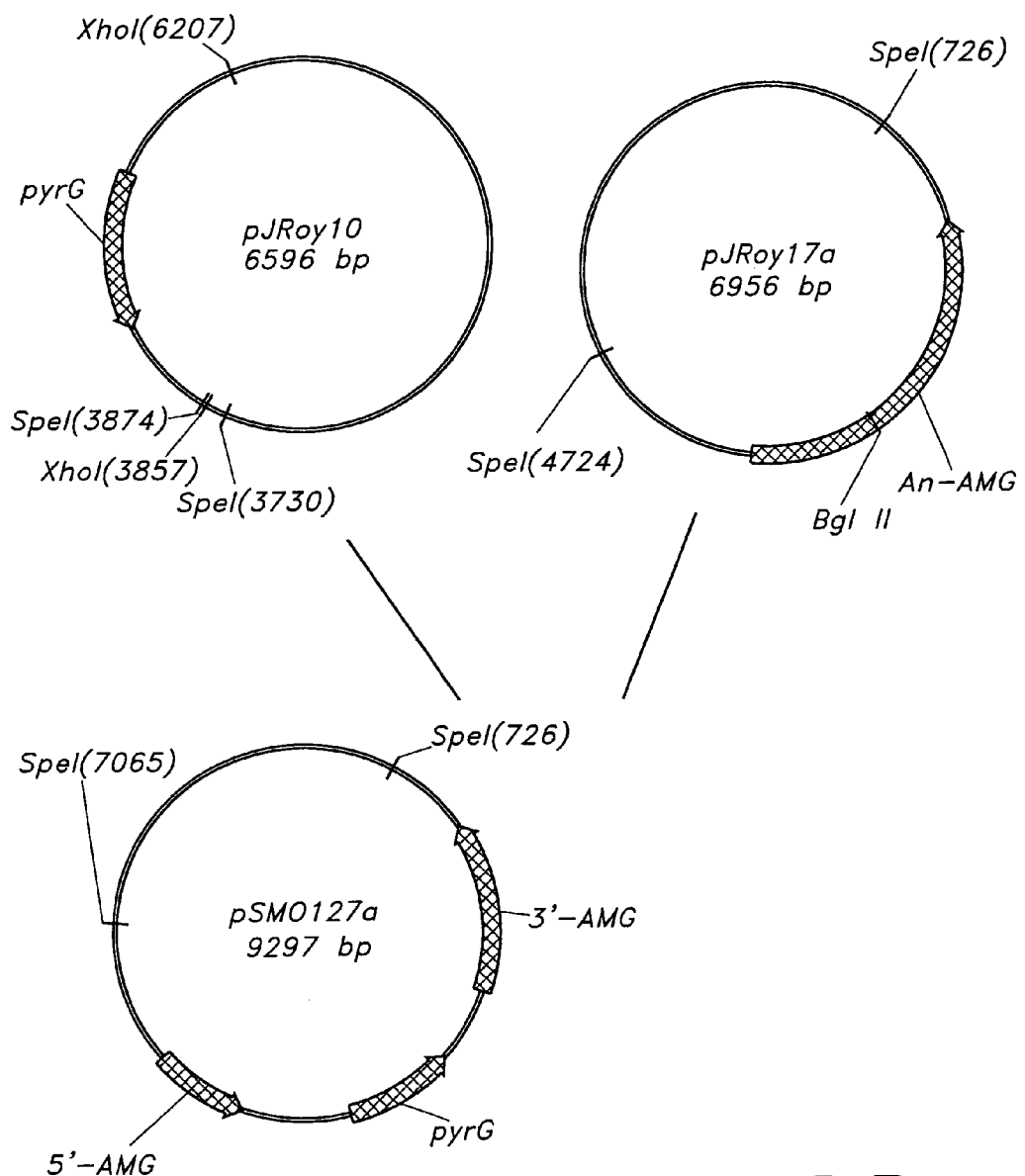
FIG. 9 shows the construction of *A. niger* disruption plasmid.

A 2.3 kb SpeI-XhoI fragment containing pyrG was gel isolated from pJRoy10 and the restricted ends filled in with Klenow polymerase. The fragment was inserted into the BglII site of pJRoy17 which cuts within the AMG gene creating plasmid pSMO127 (FIG. 9). Between the two SpeI sites of pSMO127a is contained the 2.3 kb pyrG gene flanked by 2.2 kb and 2.3 kb 5' and 3' AMG, respectively.

4. Construction of a *A. niger* Strain Disrupted for AMG, SMO110

*A. niger* JRoyP3 is a spontaneously pyrG mutant of *A. niger* BO-1, which was selected for the growth on a plate containing 5'-fluoro-orotic acid (5'-FOA). The pyrG gene encodes orotidine 5'-phosphate carboxylase and its deficient mutant can be characterized as uridine auxotroph. The identity of pyrG mutant was confirmed by the complementation of the growth on a minimal medium with *A. nidulans* pyrG gene.

Twenty micrograms of the plasmid pSMO127 was digested with SpeI. The DNA was resolved on an 0.8% agarose gel and the 6 kb consisting of the linear disruption cassette was gel isolated. The linear DNA was transformed into strain JRoyP3.

Genomic DNA was prepared from 200 transformants which was then digested with SpeI. The gel-resolved DNA was transferred to a hybond nylon filter, and hybridized to a non-radioactive DIG probe consisting of the AMG open reading frame. A gene replacement of the disruption cassette into the AMG locus would result in an increase of the wild type 4 kb AMG band to 6.3 kb, an increase due to the 2.3 kb pyrG gene. One transformant #110 with the above characteristics was selected for further analysis.

The transformant #110 were grown in 25 ml shake flasks containing YPM media. Strains BO-1 and parent strain JRoyP3 were grown as AMG producing controls. After 3 days, 30 μl of clear supernatants were run on a 8–16% SDS PAGE Novex gel. No AMG band was seen in transformant #110, while large bands of AMG were produced in the positive control strain BO-1 and parent strain JRoyP3. Transformant #110 was named SMO110.

Expression of *Talaromyces emersonii* AMG in *Aspergillus oryzae* and *Aspergillus niger*

The strains JaL228 and SMO110 was transformed with pJaL518 as described by Christensen et al.; Biotechnology 1988 6 1419–1422. Typically, *A. oryzae* mycelia was grown in a rich nutrient broth. The mycelia were separated from the broth by filtration. The enzyme preparation Novozyme® (Novo Nordisk) was added to the mycelia in osmotically stabilizing buffer such as 1.2 M $MgSO_4$ buffered to pH 5.0 with sodium phosphate. The suspension was incubated for 60 minutes at 37° C. with agitation. The protoplast was filtered through mira-cloth to remove mycelial debris. The protoplast was harvested and washed twice with STC (1.2 M sorbitol, 10 mM $CaCl_2$, 10 mM Tris-HCl pH 7.5). The protoplast was finally resuspended in 200–1000 μl STC.

For transformation 5 μg DNA was added to 100 μl protoplast suspension and then 200 μl PEG solution (60% PEG 4000, 10 mM $CaCl_2$, 10 mM Tris-HCl pH 7.5) was added and the mixture was incubated for 20 minutes at room temperature. The protoplast were harvested and washed twice with 1.2 M sorbitol. The protoplast was finally resuspended 200 μl 1.2 M sorbitol, plated on selective plates (minimal medium+10 μl Bacto-Agar (Difco), and incubated at 37° C. After 3–4 days of growth at 37° C., stable transformants appear as vigorously growing and sporulating colonies. Transformants was spore isolated twice.

Figure 10:
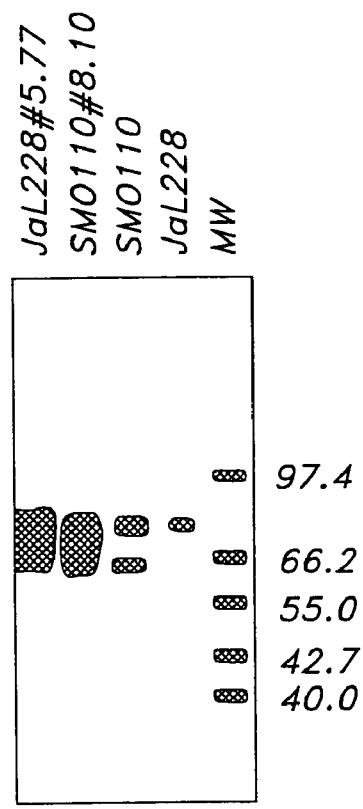
FIG. 10 shows the SDS page gel of two transformants, JaL228#5.77 and HowB112#8.10, expressing the *Talaromyces emersonii* glucoamylase of the invention. JaL228 and HowB112 are the untransformed parent strains. MW: Promega's Protein Molecular.
Figure 11:
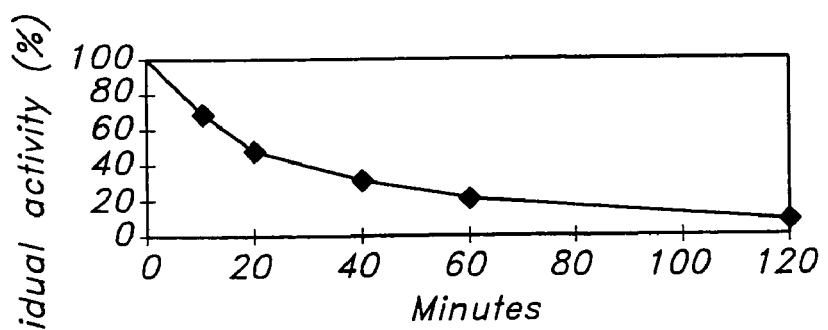
FIG. 11 shows the thermal stability of the *T. emersonii* AMG produced the strain *A. niger* HowB112 determined in 50 mM NaOAC, pH 4.5, 70° C., 0.2 AGU/ml (T½ determined to 20 minutes)

Transformants was grown in shake flask for 4 days at 30° C. in 100 ml YPM medium (2 g/l yeast extract, 2 g/l peptone, and 2% maltose). Supernatants were tested for AMG activity as described and analyzed on SDS page gel (FIG. 10).

Example 7

Removal of the Four Introns from the *Talaromyces emersonii* AMG DNA Sequence for Expression in Yeast.

For each exon a PCR reaction was made with primers containing overlap to the next exon. Tal 1 and Tal 4 contain an overlap with the yeast vector pJSO026.

Exon 1: Tal 1 was used as the 5' primer and Tal 5 as the 3' primer and the genomic sequence coding for AMG was used as the template. Exon 2: Tal 6 was used as the 5' primer and Tal 7 was used as the 3' primer and the genomic sequence coding for AMG was used as the template. Exon 3: Tal 8 was used as the 5' primer and Tal 9 was used as the 3' primer and the genomic sequence coding for AMG was used as the template. Exon 4: Tal 10 was used as the 5' primer and Tal 11 was used as the 3' primer and the genomic sequence coding for AMG was used as the template. Exon 5: Tal 12 was used as the 5' primer and Tal 4 was used as the 3' primer and the genomic sequence coding for AMG was used as the template.

A final PCR reaction was performed to combine the 5 exons to a sequence containing the complete coding sequence. In this PCR reaction the 5 fragments from the first PCR reactions were used as template and Tal 1 was used as the 5' primer and Tal4 was used as the 3' primer.

This final PCR fragment containing the coding region was used in an in vivo recombination in yeast together with pJSO026 cut with the restriction enzymes SmaI (or BamHI) and XbaI (to remove the coding region and at the same time create an overlap of about 20 bp in each end to make a recombination event possible).

```
Tal 1:
5'-CAA TAT AAA CGA CGG TAC CCG GGA  (SEQ ID NO: 23)
GAT CTC CAC CATG GCG TCC CTC GTT
G-3';

Tal 4:
5'-CTA ATT ACA TCA TGC GGC CCT CTA  (SEQ ID NO: 24)
GAT CAC TGC CAA CTA TCG TC-3';

Tal 5:
5'-AAT TTG GGT CGC TCC TGC TCG-3';   (SEQ ID NO: 25)

Tal 6:
5'-CGA GCA GGA GCG ACC CAA ATT ATT  (SEQ ID NO: 26)
TCT ACT CCT GGA CAC G-3';

Tal 7:
5'-GAT GAG ATA GTT CGC ATA CG-3';    (SEQ ID NO: 27)

Tal 8:
5'-CGT ATG CGA ACT ATC TCA TCG ACA  (SEQ ID NO: 28)
ACG GCG AGG CTT CGA CTG C-3';

Tal 9:
5'-CGA AGG TGG ATG AGT TCC AG-3';    (SEQ ID NO: 29)

Tal 10:
5'-CTG GAA CTC ATC CAC CTT CGA CCT  (SEQ ID NO: 30)
CTG GGA AGA AGT AGA AGG-3'

Tal 11:
5'-GAC AAT ACT CAG ATA TCC ATC-3'    (SEQ ID NO: 31)

Tal 12:
5'-GAT GGA TAT CTG AGT ATT GTC GAG  (SEQ ID NO: 32)
AAA TAT ACT CCC TCA GAC G-3'
```

Example 8

Expression of *Talaromyces emersonii* Glucoamylase in Yeast

To express *Talaromyces emersonii* AMG in the yeast *Saccharomyces cerevisiae* YNG318 the yeast expression vector pJSO26 was constructed as described in the "Material and Methods" section above.

PJSO26 comprising the DNA sequence encoding the *Talaromyces* AMG was transformed into the yeast by standard methods (cf. Sambrooks et al., (1989), Molecular Cloning: A Laboratory Manual, 2nd Ed., Cold Spring Harbor).

The yeast cells were grown at 30° C. for 3 days in Sc-ura medium followed by growth for 3 days in YPD. The culture was then centrifuged and the supernatant was used for the thermostability assay described in the "Materials and Method" section.

Thermal Stability of the *Talaromyces* AMG Expressed in Yeast at 68° C.

Figure 12:
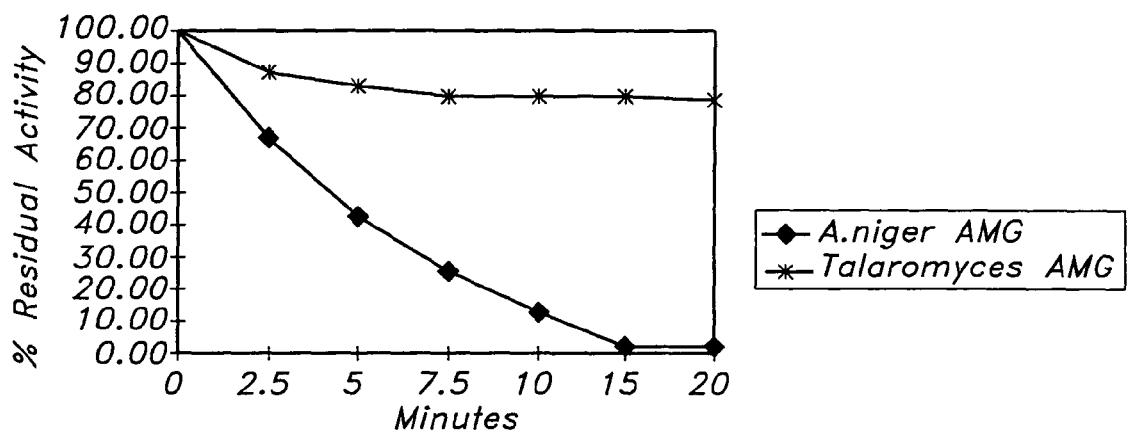
FIG. 12 compares the thermal stability at 68° C. of the fermentation broth of *T. emersonii* AMG expressed in yeast produced in yeast and the *A. niger* AMG.

The fermentation broth of the *Talaromyces emersonii* AMG expressed in yeast (*Saccharomyces cerevisiae* YNG318) was used for determination of the thermal stability at 68° C. using the method described above under "Determination of thermal stability II". The result of the test is shown in FIG. 12.

Example 9

Purification of Recombinant *Talaromyces* AMG Produced Using *A. Niqer* HowB112

200 ml culture broth from fermentation of *A. niger* HowB112 harboring the *Talaromyces emersonii* gene was centrifuged at 9000 rpm and dialyzed against 20 mM NaOac, pH 5 over night. The solution was then applied on a S Sepharose column (200 ml) previously equilibrated in 20 mM NaOAc, pH 5. The glucoamylase was collected in the effluent, and applied on a Q Sepharose column (50 ml) previously equilibrated in 20 mM NaOAC, pH 4.5. Unbound material was washed of the column and the glucoamylase was eluted using a linear gradient from 0–0.3 M NaCl in 20 mM NaOAc over 10 column volumes. Purity of the glucoamylase fraction was checked by SDS-PAGE and only one single band was seen. The molecular weight was again found to about 70 kdal as seen for the wild type glucoamylase. The specific activity towards maltose was measured and a specific activity of 8.0 AGU/mg (37° C.) and 21.0 AGU/mg (60° C.) were found which is in accordance the data on the wild type enzyme.

Example 10

Kinetic Parameters
Kinetic Parameters for Hydrolysis of Maltose and Isomaltose by *Aspergillus niger* AMG and the recombinant *Talaromyces emersonii* AMG expressed in *A. niger*.

| | $k_{cat}$ (s$^{-1}$)$^a$ | $K_m$ (mM) | $k_{cat}/K_m$ (s$^{-1}$mM$^{-1}$) |
|---|---|---|---|
| Maltose | | | |
| *Talaromyces emersonii* | 30.6 | 3.8 | 8.1 |
| *Aspergillus niger* | 10.7 | 1.2 | 8.8 |

-continued

Kinetic Parameters
Kinetic Parameters for Hydrolysis of Maltose and Isomaltose by *Aspergillus niger* AMG and the recombinant *Talaromyces emersonii* AMG expressed in *A. niger*.

| | $k_{cat}$ (s$^{-1}$)$^a$ | $K_m$ (mM) | $k_{cat}/K_m$ (s$^{-1}$mM$^{-1}$) |
|---|---|---|---|
| Isomaltose | | | |
| *Talaromyces emersonii* | 2.70 | 53.6 | 0.050 |
| *Aspergillus niger* | 0.41 | 19.8 | 0.021 |

$^a$At 45° C. uusing 0.05 M NaOAc, pH 4.5

Example 11

Saccharification Performance of Recombinant *Talaromyces emersonii* AMG Produced in *A. niqer*

The saccharification performance of the *Talaromyces emersonii* glucoamylase was tested at different temperatures with and without the addition of acid α-amylase and pullulanase. Saccharification was run under the following conditions:

Substrate: 10 DE Maltodextrin, approx. 30% DS (w/w)
Temperatures: 60, 65, or 70° C.
Initial pH: 4.5
Enzyme dosage:
Recombinant *Talaromyces emersonii* glucoamylase produced in *A. niger* 0.24 or 0.32 AGU/g DS
Acid α-amylase derived from *A. niger* 0.020 AFAU/g DS
Pullulanase derived from Bacillus: 0.03 PUN/g DS
When used alone Talaromyces AMG was dosed at the high dosage (0.32 AGU/g DS), otherwise at the low dosage, i.e., 0.24 AGU/g DS.

Saccharification

The substrate for saccharificationg was made by dissolving maltodextrin (prepared from common corn) in boiling Milli-Q water and adjusting the dry substance to approximately 30% (w/w). pH was adjusted to 4.5 (measured at 60° C.). Aliquots of substrate corresponding to 150 g dry solids were transferred to 500 ml blue cap glass flasks and placed in a water bath with stirring at the respective temperatures. Enzymes were added and pH readjusted if necessary (measured at incubation temperature). Samples were taken periodically and analysed at HPLC for determination of the carbohydrate composition.

The glucose produced during saccharification are given in the table below, the first three columns representing the saccharification with glucoamylase and acid α-amylase and pullulanase, the last three with glucoamylase alone. Numbers are % DP1 on DS.

| | 0.24 AGU + 0.02 AFAU + 0.03 PUN | | | 0.32 AGU | | |
|---|---|---|---|---|---|---|
| Time (hours) | 60° C. | 65° C. | 70° C. | 60° C. | 65° C. | 70° C. |
| 24 | 88.96 | 90.51 | 87.91 | 84.98 | 86.28 | 84.35 |
| 48 | 94.03 | 94.28 | 91.90 | 88.86 | 89.51 | 86.98 |
| 72 | 95.08 | 94.75 | 93.12 | 90.18 | 90.42 | 87.99 |
| 98 | 95.03 | 94.59 | 93.64 | 90.65 | 90.72 | 88.51 |

A glucose yield above 95% was obtained after 72 hours using an enzyme dosage of 0.24 AGU/g DS which is corresponding to 0.03 mg/g DS. The typical dosage of *A.*

*niger* AMG would be 0.18 AGU/g DS which is corresponding to 0.09 mg/g DS to get a yield og 95–96% glucose. A significantly lower enzyme dosage on mg enzyme protein of *Talaromyces* AMG is therefore required in the saccharification process compared to *A. niger* AMG due to the high specific activity of *T. emersonii* AMG.

Example 12

Temperature Stability—T½ (Half-Life) of Recombinant *Talaromyces emersonii* AMG Expressed in Yeast The thermal stability of recombinant *Talaromyces emersonii* glucoamylase expressed in yeast (purified using the method described in Example 9) was determined at 70° C., pH 4.5, 0.2 AGU/ml using the method described above in the "Material and Methods" section as "Thermal Stability I (T½ (half-life) determination of AMG".

Figure 13:
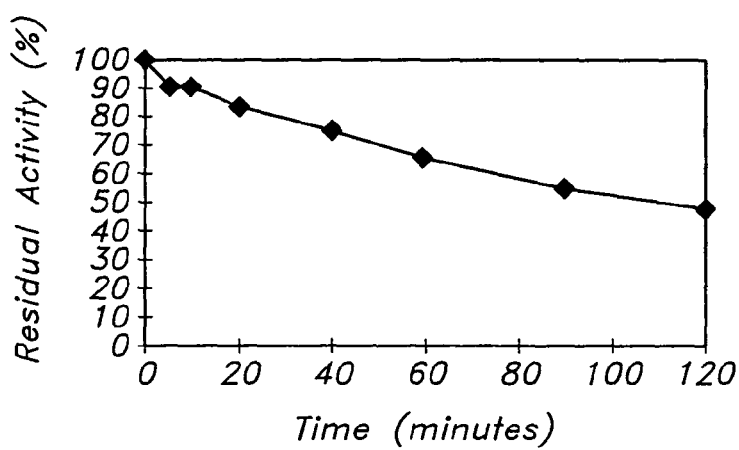
FIG. 13 shows the result of the test for determining the thermostability of recombinant *Talaromyces emersonii* AMG produced in yeast at 70° C., pH 4.5, 0.2 AGU/ml. T½ was determined to about 110° C.

FIG. 13 shows the result of the test. The T½ of the recombinant *Talaromyces emersonii* glucoamylase expressed in yeast was determined to about 110 minutes at 70° C.

The invention claimed is:

1. A process for saccharifying starch, said process comprising contacting starch or partially hydrolyzed starch with a glucoamylase which has an amino acid sequence that has at least 95% identity with SEQ ID NO:7, under conditions that result in saccharification.

2. The process of claim 1, wherein said glucoamylase is present in the range from 0.05 to 0.5 AGU per gram of dry solids.

3. The process of claim 1, wherein said starch or partially hydrolyzed starch comprises at least 30 percent by weight of dry solids.

4. The process of claim 1, further comprising contacting said starch or partially hydrolyzed starch with a debranching enzyme selected from the group of pullulanase and isoamylase.

5. The process of claim 1, wherein the contacting is conducted at a pH of about 3 to 5.5 and at a temperature of 60–80° C.

6. The process of claim 1, wherein said glucoamylase is derived from *Talaromyces emersonii*.

7. The process of claim 1, further comprising contacting said starch solution with an acidic alpha-amylase.

8. The process of claim 7, wherein said acidic alpha-amylase is derived from *Aspergillus niger*.

9. The process of claim 1, wherein the glucoamylase has an amino acid sequence of SEQ ID NO:7.

10. The process of claim 1, wherein the glucoamylase has an amino acid sequence that is at least 97% identical with SEQ ID NO:7.

11. The process of claim 1, wherein the glucoamylase has an amino acid sequence that is at least 99% identical with SEQ ID NO:7.

12. A process for saccharifying liquidified starch solution, which method comprising contacting said starch solution with a glucoamylase which has an amino acid sequence that has at least 95% identity with SEQ ID NO:7.

13. The process of claim 9, wherein the glucoamylase has an amino acid sequence of SEQ ID NO:7.

14. The process of claim 12, wherein the glucoamylase has an amino acid sequence that is at least 97% identical with SEQ ID NO:7.

15. The process of claim 12, wherein the glucoamylase has an amino acid sequence that is at least 99% identical with SEQ ID NO:7.

* * * * *

```
                           SEQUENCE LISTING

<160> NUMBER OF SEQ ID NOS: 34

<210> SEQ ID NO 1
<211> LENGTH: 25
<212> TYPE: PRT
<213> ORGANISM: Talaromyces emersonii
<220> FEATURE:
<221> NAME/KEY: UNSURE
<222> LOCATION: (0)...(0)
<223> OTHER INFORMATION: Xaa at position 13 denotes a residue that could
                         not be assigned

<400> SEQUENCE: 1

Ala Asn Gly Ser Leu Asp Ser Phe Leu Ala Thr Glu Xaa Pro Ile Ala
  1               5                  10                  15

Leu Gln Gly Val Leu Asn Asn Ile Gly
             20                  25

<210> SEQ ID NO 2
<211> LENGTH: 20
<212> TYPE: PRT
<213> ORGANISM: Talaromyces emersonii

<400> SEQUENCE: 2

Val Gln Thr Ile Ser Asn Pro Ser Gly Asp Leu Ser Thr Gly Gly Leu
  1               5                  10                  15

Gly Glu Pro Lys
             20

<210> SEQ ID NO 3
<211> LENGTH: 22
<212> TYPE: PRT
<213> ORGANISM: Talaromyces emersonii
<220> FEATURE:
<221> NAME/KEY: UNSURE
<222> LOCATION: (0)...(0)
<223> OTHER INFORMATION: Xaa at positions 1 and 12 denotes a residue
                         that could not be assigned

<400> SEQUENCE: 3

Xaa Asn Val Asn Glu Thr Ala Phe Thr Gly Pro Xaa Gly Arg Pro Gln
  1               5                  10                  15

Arg Asp Gly Pro Ala Leu
             20

<210> SEQ ID NO 4
<211> LENGTH: 35
<212> TYPE: PRT
<213> ORGANISM: Talaromyces emersonii

<400> SEQUENCE: 4
```

```
Asp Val Asn Ser Ile Leu Gly Ser Ile His Thr Phe Asp Pro Ala Gly
1               5                   10                  15

Gly Cys Asp Asp Ser Thr Phe Gln Pro Cys Ser Ala Arg Ala Leu Ala
            20                  25                  30

Asn His Lys
        35

<210> SEQ ID NO 5
<211> LENGTH: 16
<212> TYPE: PRT
<213> ORGANISM: Talaromyces emersonii
<220> FEATURE:
<221> NAME/KEY: UNSURE
<222> LOCATION: (0)...(0)
<223> OTHER INFORMATION: Xaa at position 2 denotes a residue that could
                         not be assigned

<400> SEQUENCE: 5

Thr Xaa Ala Ala Ala Glu Gln Leu Tyr Asp Ala Ile Tyr Gln Trp Lys
1               5                   10                  15

<210> SEQ ID NO 6
<211> LENGTH: 35
<212> TYPE: PRT
<213> ORGANISM: Talaromyces emersonii

<400> SEQUENCE: 6

Ala Gln Thr Asp Gly Thr Ile Val Trp Glu Asp Asp Pro Asn Arg Ser
1               5                   10                  15

Tyr Thr Val Pro Ala Tyr Cys Gly Gln Thr Thr Ala Ile Leu Asp Asp
            20                  25                  30

Ser Trp Gln
        35

<210> SEQ ID NO 7
<211> LENGTH: 591
<212> TYPE: PRT
<213> ORGANISM: Talaromyces emersonii

<400> SEQUENCE: 7

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Asn Arg Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95

Ser Gly Asp Leu Ser Thr Gly Gly Leu Gly Glu Pro Lys Phe Asn Val
            100                 105                 110

Asn Glu Thr Ala Phe Thr Gly Pro Trp Gly Arg Pro Gln Arg Asp Gly
        115                 120                 125

Pro Ala Leu Arg Ala Thr Ala Leu Ile Ala Tyr Ala Asn Tyr Leu Ile
    130                 135                 140

Asp Asn Gly Glu Ala Ser Thr Ala Asp Glu Ile Ile Trp Pro Ile Val
145                 150                 155                 160
```

-continued

```
Gln Asn Asp Leu Ser Tyr Ile Thr Gln Tyr Trp Asn Ser Ser Thr Phe
                165                 170                 175
Asp Leu Trp Glu Glu Val Glu Gly Ser Ser Phe Phe Thr Thr Ala Val
            180                 185                 190
Gln His Arg Ala Leu Val Glu Gly Asn Ala Leu Ala Thr Arg Leu Asn
        195                 200                 205
His Thr Cys Ser Asn Cys Val Ser Gln Ala Pro Gln Val Leu Cys Phe
    210                 215                 220
Leu Gln Ser Tyr Trp Thr Gly Ser Tyr Val Leu Ala Asn Phe Gly Gly
225                 230                 235                 240
Ser Gly Arg Ser Gly Lys Asp Val Asn Ser Ile Leu Gly Ser Ile His
                245                 250                 255
Thr Phe Asp Pro Ala Gly Gly Cys Asp Ser Thr Phe Gln Pro Cys
            260                 265                 270
Ser Ala Arg Ala Leu Ala Asn His Lys Val Val Thr Asp Ser Phe Arg
        275                 280                 285
Ser Ile Tyr Ala Ile Asn Ser Gly Ile Ala Glu Gly Ser Ala Val Ala
    290                 295                 300
Val Gly Arg Tyr Pro Glu Asp Val Tyr Gln Gly Gly Asn Pro Trp Tyr
305                 310                 315                 320
Leu Ala Thr Ala Ala Ala Ala Glu Gln Leu Tyr Asp Ala Ile Tyr Gln
                325                 330                 335
Trp Lys Lys Ile Gly Ser Ile Ser Ile Thr Asp Val Ser Leu Pro Phe
            340                 345                 350
Phe Gln Asp Ile Tyr Pro Ser Ala Ala Val Gly Thr Tyr Asn Ser Gly
        355                 360                 365
Ser Thr Thr Phe Asn Asp Ile Ile Ser Ala Val Gln Thr Tyr Gly Asp
    370                 375                 380
Gly Tyr Leu Ser Ile Val Glu Lys Tyr Thr Pro Ser Asp Gly Ser Leu
385                 390                 395                 400
Thr Glu Gln Phe Ser Arg Thr Asp Gly Thr Pro Leu Ser Ala Ser Ala
                405                 410                 415
Leu Thr Trp Ser Tyr Ala Ser Leu Leu Thr Ala Ser Ala Arg Arg Gln
            420                 425                 430
Ser Val Val Pro Ala Ser Trp Gly Glu Ser Ser Ala Ser Ser Val Leu
        435                 440                 445
Ala Val Cys Ser Ala Thr Ser Ala Thr Gly Pro Tyr Ser Thr Ala Thr
    450                 455                 460
Asn Thr Val Trp Pro Ser Ser Gly Ser Gly Ser Ser Thr Thr Thr Ser
465                 470                 475                 480
Ser Ala Pro Cys Thr Thr Pro Thr Ser Val Ala Val Thr Phe Asp Glu
                485                 490                 495
Ile Val Ser Thr Ser Tyr Gly Glu Thr Ile Tyr Leu Ala Gly Ser Ile
            500                 505                 510
Pro Glu Leu Gly Asn Trp Ser Thr Ala Ser Ala Ile Pro Leu Arg Ala
        515                 520                 525
Asp Ala Tyr Thr Asn Ser Asn Pro Leu Trp Tyr Val Thr Val Asn Leu
    530                 535                 540
Pro Pro Gly Thr Ser Phe Glu Tyr Lys Phe Phe Lys Asn Gln Thr Asp
545                 550                 555                 560
Gly Thr Ile Val Trp Glu Asp Pro Asn Arg Ser Tyr Thr Val Pro
                565                 570                 575
```

```
                Ala Tyr Cys Gly Gln Thr Thr Ala Ile Leu Asp Asp Ser Trp Gln
                            580                 585                 590

<210> SEQ ID NO 8
<211> LENGTH: 1605
<212> TYPE: DNA
<213> ORGANISM: Aspergillus niger
<220> FEATURE:
<221> NAME/KEY: CDS
<222> LOCATION: (1)...(1602)
<220> FEATURE:
<221> NAME/KEY: sig_peptide
<222> LOCATION: (1)...(72)
<220> FEATURE:
<221> NAME/KEY: mat_peptide
<222> LOCATION: (73)...(1602)

<400> SEQUENCE: 8 atg tcg ttc cga tct cta ctc gcc ctg agc ggc ctc gtc tgc aca ggg         48
Met Ser Phe Arg Ser Leu Leu Ala Leu Ser Gly Leu Val Cys Thr Gly
                -20                 -15                 -10 ttg gca aat gtg att tcc aag cgc gcg acc ttg gat tca tgg ttg agc         96
Leu Ala Asn Val Ile Ser Lys Arg Ala Thr Leu Asp Ser Trp Leu Ser
            -5                   1               5 aac gaa gcg acc gtg gct cgt act gcc atc ctg aat aac atc ggg gcg        144
Asn Glu Ala Thr Val Ala Arg Thr Ala Ile Leu Asn Asn Ile Gly Ala
         10                  15                  20 gac ggt gct tgg gtg tcg ggc gcg gac tct ggc att gtc gtt gct agt        192
Asp Gly Ala Trp Val Ser Gly Ala Asp Ser Gly Ile Val Val Ala Ser
 25                  30                  35                  40 ccc agc acg gat aac ccg gac tac ttc tac acc tgg act cgc gac tct        240
Pro Ser Thr Asp Asn Pro Asp Tyr Phe Tyr Thr Trp Thr Arg Asp Ser
                 45                  50                  55 ggt ctc gtc ctc aag acc ctc gtc gat ctc ttc cga aat gga gat acc        288
Gly Leu Val Leu Lys Thr Leu Val Asp Leu Phe Arg Asn Gly Asp Thr
             60                  65                  70 agt ctc ctc tcc acc att gag aac tac atc tcc gcc cag gca att gtc        336
Ser Leu Leu Ser Thr Ile Glu Asn Tyr Ile Ser Ala Gln Ala Ile Val
         75                  80                  85 cag ggt atc agt aac ccc tct ggt gat ctg tcc agc ggc gct ggt ctc        384
Gln Gly Ile Ser Asn Pro Ser Gly Asp Leu Ser Ser Gly Ala Gly Leu
 90                  95                 100 ggt gaa ccc aag ttc aat gtc gat gag act gcc tac act ggt tct tgg        432
Gly Glu Pro Lys Phe Asn Val Asp Glu Thr Ala Tyr Thr Gly Ser Trp
105                 110                 115                 120 gga cgg ccg cag cga gat ggt ccg gct ctg aga gca act gct atg atc        480
Gly Arg Pro Gln Arg Asp Gly Pro Ala Leu Arg Ala Thr Ala Met Ile
                125                 130                 135 ggc ttc ggg cag tgg ctg ctt gac aat ggc tac acc agc acc gca acg        528
Gly Phe Gly Gln Trp Leu Leu Asp Asn Gly Tyr Thr Ser Thr Ala Thr
            140                 145                 150 gac att gtt tgg ccc ctc gtt agg aac gac ctg tcg tat gtg gct caa        576
Asp Ile Val Trp Pro Leu Val Arg Asn Asp Leu Ser Tyr Val Ala Gln
        155                 160                 165 tac tgg aac cag aca gga tat gat ctc tgg gaa gaa gtc aat ggc tcg        624
Tyr Trp Asn Gln Thr Gly Tyr Asp Leu Trp Glu Glu Val Asn Gly Ser
    170                 175                 180 tct ttc ttt acg att gct gtg caa cac cgc gcc ctt gtc gaa ggt agt        672
Ser Phe Phe Thr Ile Ala Val Gln His Arg Ala Leu Val Glu Gly Ser
185                 190                 195                 200 gcc ttc gcg acg gcc gtc ggc tcg tcc tgc tcc tgg tgt gat tct cag        720
Ala Phe Ala Thr Ala Val Gly Ser Ser Cys Ser Trp Cys Asp Ser Gln
                205                 210                 215
```

-continued

| | |
|---|---|
| gca ccc gaa att ctc tgc tac ctg cag tcc ttc tgg acc ggc agc ttc<br>Ala Pro Glu Ile Leu Cys Tyr Leu Gln Ser Phe Trp Thr Gly Ser Phe<br>    220                 225                 230 | 768 |
| att ctg gcc aac ttc gat agc agc cgt tcc ggc aag gac gca aac acc<br>Ile Leu Ala Asn Phe Asp Ser Ser Arg Ser Gly Lys Asp Ala Asn Thr<br>235                 240                 245 | 816 |
| ctc ctg gga agc atc cac acc ttt gat cct gag gcc gca tgc gac gac<br>Leu Leu Gly Ser Ile His Thr Phe Asp Pro Glu Ala Ala Cys Asp Asp<br>    250                 255                 260 | 864 |
| tcc acc ttc cag ccc tgc tcc ccg cgc gcg ctc gcc aac cac aag gag<br>Ser Thr Phe Gln Pro Cys Ser Pro Arg Ala Leu Ala Asn His Lys Glu<br>265                 270                 275                 280 | 912 |
| gtt gta gac tct ttc cgc tca atc tat acc ctc aac gat ggt ctc agt<br>Val Val Asp Ser Phe Arg Ser Ile Tyr Thr Leu Asn Asp Gly Leu Ser<br>                285                 290                 295 | 960 |
| gac agc gag gct gtt gcg gtg ggt cgg tac cct gag gac acg tac tac<br>Asp Ser Glu Ala Val Ala Val Gly Arg Tyr Pro Glu Asp Thr Tyr Tyr<br>    300                 305                 310 | 1008 |
| aac ggc aac ccg tgg ttc ctg tgc acc ttg gct gcc gca gag cag ttg<br>Asn Gly Asn Pro Trp Phe Leu Cys Thr Leu Ala Ala Ala Glu Gln Leu<br>315                 320                 325 | 1056 |
| tac gat gct cta tac cag tgg gac aag cag ggg tcg ttg gag gtc aca<br>Tyr Asp Ala Leu Tyr Gln Trp Asp Lys Gln Gly Ser Leu Glu Val Thr<br>    330                 335                 340 | 1104 |
| gat gtg tcg ctg gac ttc ttc aag gca ctg tac agc gat gct gct act<br>Asp Val Ser Leu Asp Phe Phe Lys Ala Leu Tyr Ser Asp Ala Ala Thr<br>345                 350                 355                 360 | 1152 |
| ggc acc tac tct tcg tcc agt tcg act tat agt agc att gta gat gcc<br>Gly Thr Tyr Ser Ser Ser Ser Thr Tyr Ser Ser Ile Val Asp Ala<br>                365                 370                 375 | 1200 |
| gtg aag act ttc gcc gat ggc ttc gtc tct att gtg gaa act cac gcc<br>Val Lys Thr Phe Ala Asp Gly Phe Val Ser Ile Val Glu Thr His Ala<br>    380                 385                 390 | 1248 |
| gca agc aac ggc tcc atg tcc gag caa tac gac aag tct gat ggc gag<br>Ala Ser Asn Gly Ser Met Ser Glu Gln Tyr Asp Lys Ser Asp Gly Glu<br>395                 400                 405 | 1296 |
| cag ctt tcc gct cgc gac ctg acc tgg tct tat gct gct ctg ctg acc<br>Gln Leu Ser Ala Arg Asp Leu Thr Trp Ser Tyr Ala Ala Leu Leu Thr<br>    410                 415                 420 | 1344 |
| gcc aac aac cgt cgt aac tcc gtc gtg cct gct tct tgg ggc gag acc<br>Ala Asn Asn Arg Arg Asn Ser Val Val Pro Ala Ser Trp Gly Glu Thr<br>425                 430                 435                 440 | 1392 |
| tct gcc agc agc gtg ccc ggc acc tgt gcg gcc aca tct gcc att ggt<br>Ser Ala Ser Ser Val Pro Gly Thr Cys Ala Ala Thr Ser Ala Ile Gly<br>                445                 450                 455 | 1440 |
| acc tac agc agt gtg act gtc acc tcg tgg ccg agt atc gtg gct act<br>Thr Tyr Ser Ser Val Thr Val Thr Ser Trp Pro Ser Ile Val Ala Thr<br>    460                 465                 470 | 1488 |
| ggc ggc acc act acg acg gct acc ccc act gga tcc ggc agc gtg acc<br>Gly Gly Thr Thr Thr Thr Ala Thr Pro Thr Gly Ser Gly Ser Val Thr<br>475                 480                 485 | 1536 |
| tcg acc agc aag acc acc gcg act gct agc aag acc agc acc acc acc<br>Ser Thr Ser Lys Thr Thr Ala Thr Ala Ser Lys Thr Ser Thr Thr Thr<br>    490                 495                 500 | 1584 |
| cgc tct ggt atg tca ctg tga<br>Arg Ser Gly Met Ser Leu<br>505                 510 | 1605 |

<210> SEQ ID NO 9

<211> LENGTH: 534
<212> TYPE: PRT
<213> ORGANISM: Aspergillus niger
<220> FEATURE:
<221> NAME/KEY: SIGNAL
<222> LOCATION: (1)...(24)

<400> SEQUENCE: 9

```
Met Ser Phe Arg Ser Leu Leu Ala Leu Ser Gly Leu Val Cys Thr Gly
                -20                 -15                 -10

Leu Ala Asn Val Ile Ser Lys Arg Ala Thr Leu Asp Ser Trp Leu Ser
            -5                   1               5

Asn Glu Ala Thr Val Ala Arg Thr Ala Ile Leu Asn Asn Ile Gly Ala
         10                  15                  20

Asp Gly Ala Trp Val Ser Gly Ala Asp Ser Gly Ile Val Val Ala Ser
 25                  30                  35                  40

Pro Ser Thr Asp Asn Pro Asp Tyr Phe Tyr Thr Trp Thr Arg Asp Ser
                 45                  50                  55

Gly Leu Val Leu Lys Thr Leu Val Asp Leu Phe Arg Asn Gly Asp Thr
                 60                  65                  70

Ser Leu Leu Ser Thr Ile Glu Asn Tyr Ile Ser Ala Gln Ala Ile Val
             75                  80                  85

Gln Gly Ile Ser Asn Pro Ser Gly Asp Leu Ser Ser Gly Ala Gly Leu
 90                  95                 100

Gly Glu Pro Lys Phe Asn Val Asp Glu Thr Ala Tyr Thr Gly Ser Trp
105                 110                 115                 120

Gly Arg Pro Gln Arg Asp Gly Pro Ala Leu Arg Ala Thr Ala Met Ile
                125                 130                 135

Gly Phe Gly Gln Trp Leu Leu Asp Asn Gly Tyr Thr Ser Thr Ala Thr
            140                 145                 150

Asp Ile Val Trp Pro Leu Val Arg Asn Asp Leu Ser Tyr Val Ala Gln
                155                 160                 165

Tyr Trp Asn Gln Thr Gly Tyr Asp Leu Trp Glu Glu Val Asn Gly Ser
170                 175                 180

Ser Phe Phe Thr Ile Ala Val Gln His Arg Ala Leu Val Glu Gly Ser
185                 190                 195                 200

Ala Phe Ala Thr Ala Val Gly Ser Ser Cys Ser Trp Cys Asp Ser Gln
                205                 210                 215

Ala Pro Glu Ile Leu Cys Tyr Leu Gln Ser Phe Trp Thr Gly Ser Phe
            220                 225                 230

Ile Leu Ala Asn Phe Asp Ser Ser Arg Ser Gly Lys Asp Ala Asn Thr
                235                 240                 245

Leu Leu Gly Ser Ile His Thr Phe Asp Pro Glu Ala Ala Cys Asp Asp
        250                 255                 260

Ser Thr Phe Gln Pro Cys Ser Pro Arg Ala Leu Ala Asn His Lys Glu
265                 270                 275                 280

Val Val Asp Ser Phe Arg Ser Ile Tyr Thr Leu Asn Asp Gly Leu Ser
                285                 290                 295

Asp Ser Glu Ala Val Ala Val Gly Arg Tyr Pro Glu Asp Thr Tyr Tyr
            300                 305                 310

Asn Gly Asn Pro Trp Phe Leu Cys Thr Leu Ala Ala Ala Glu Gln Leu
        315                 320                 325

Tyr Asp Ala Leu Tyr Gln Trp Asp Lys Gln Gly Ser Leu Glu Val Thr
330                 335                 340

Asp Val Ser Leu Asp Phe Phe Lys Ala Leu Tyr Ser Asp Ala Ala Thr
```

```
                345                 350                 355                 360

Gly Thr Tyr Ser Ser Ser Ser Thr Tyr Ser Ile Val Asp Ala
                365                     370                 375

Val Lys Thr Phe Ala Asp Gly Phe Val Ser Ile Val Glu Thr His Ala
            380                     385                 390

Ala Ser Asn Gly Ser Met Ser Glu Gln Tyr Asp Lys Ser Asp Gly Glu
            395                 400                 405

Gln Leu Ser Ala Arg Asp Leu Thr Trp Ser Tyr Ala Ala Leu Leu Thr
        410                 415                 420

Ala Asn Asn Arg Arg Asn Ser Val Val Pro Ala Ser Trp Glu Thr
425                 430                 435                 440

Ser Ala Ser Ser Val Pro Gly Thr Cys Ala Ala Thr Ser Ala Ile Gly
                445                 450                 455

Thr Tyr Ser Ser Val Thr Val Thr Ser Trp Pro Ser Ile Val Ala Thr
                460                 465                 470

Gly Gly Thr Thr Thr Thr Ala Thr Pro Thr Gly Ser Gly Ser Val Thr
            475                 480                 485

Ser Thr Ser Lys Thr Thr Ala Thr Ala Ser Lys Thr Ser Thr Thr Thr
        490                 495                 500

Arg Ser Gly Met Ser Leu
505                 510

<210> SEQ ID NO 10
<211> LENGTH: 17
<212> TYPE: DNA
<213> ORGANISM: Artificial Sequence
<220> FEATURE:
<223> OTHER INFORMATION: Primer 102434
                N= A, G, C or T

<400> SEQUENCE: 10
gtnttraaya ayathgg                                                        17

<210> SEQ ID NO 11
<211> LENGTH: 17
<212> TYPE: DNA
<213> ORGANISM: Artificial Sequence
<220> FEATURE:
<223> OTHER INFORMATION: Primer 102435
                N = A, G, C, or T

<400> SEQUENCE: 11
gtnctnaaya ayathgg                                                        17

<210> SEQ ID NO 12
<211> LENGTH: 17
<212> TYPE: DNA
<213> ORGANISM: Artificial Sequence
<220> FEATURE:
<223> OTHER INFORMATION: Primer 117360
                N= A, G, C or T

<400> SEQUENCE: 12
ctrganaccc tyctyca                                                        17

<210> SEQ ID NO 13
<211> LENGTH: 17
<212> TYPE: DNA
<213> ORGANISM: Artificial Sequence
<220> FEATURE:
<223> OTHER INFORMATION: Primer 117361
```

```
<400> SEQUENCE: 13
ctraayaccc tyctyca                                                          17

<210> SEQ ID NO 14
<211> LENGTH: 17
<212> TYPE: DNA
<213> ORGANISM: Artificial Sequence
<220> FEATURE:
<223> OTHER INFORMATION: Primer 127420
                  N= A, G, C or T

<400> SEQUENCE: 14
accctyctrc trggntt                                                          17

<210> SEQ ID NO 15
<211> LENGTH: 20
<212> TYPE: DNA
<213> ORGANISM: Artificial Sequence
<220> FEATURE:
<223> OTHER INFORMATION: Primer 123036

<400> SEQUENCE: 15
gtgagcccaa gttcaatgtg                                                       20

<210> SEQ ID NO 16
<211> LENGTH: 21
<212> TYPE: DNA
<213> ORGANISM: Artificial Sequence
<220> FEATURE:
<223> OTHER INFORMATION: Primer 1

<400> SEQUENCE: 16
agaaatcggg tatcctttca                                                       21

<210> SEQ ID NO 17
<211> LENGTH: 105
<212> TYPE: DNA
<213> ORGANISM: Artificial Sequence
<220> FEATURE:
<223> OTHER INFORMATION: Primer 2

<400> SEQUENCE: 17
gctcctcatg gtggatcccc agttgtgtat atagaggatt gaggaaggaa gagaagtgtg           60
gatagaggta aattgagttg gaaactccaa gcatggcatc cttgc                          105

<210> SEQ ID NO 18
<211> LENGTH: 30
<212> TYPE: DNA
<213> ORGANISM: Artificial Sequence
<220> FEATURE:
<223> OTHER INFORMATION: Primer 139746

<400> SEQUENCE: 18
gacagatctc caccatggcg ccctcgttg                                             30

<210> SEQ ID NO 19
<211> LENGTH: 27
<212> TYPE: DNA
<213> ORGANISM: Artificial Sequence
<220> FEATURE:
<223> OTHER INFORMATION: Primer 3

<400> SEQUENCE: 19
gacctcgagt cactgccaac atcgtc                                                27
```

<210> SEQ ID NO 20
<211> LENGTH: 29
<212> TYPE: DNA
<213> ORGANISM: Artificial Sequence
<220> FEATURE:
<223> OTHER INFORMATION: Primer 4

<400> SEQUENCE: 20
ccctcaccag gggaatgctg agttgatg                               29

<210> SEQ ID NO 21
<211> LENGTH: 18
<212> TYPE: DNA
<213> ORGANISM: Artificial Sequence
<220> FEATURE:
<223> OTHER INFORMATION: Primer 950847

<400> SEQUENCE: 21
cgccattctc ggcgactt                                          18

<210> SEQ ID NO 22
<211> LENGTH: 18
<212> TYPE: DNA
<213> ORGANISM: Artificial Sequence
<220> FEATURE:
<223> OTHER INFORMATION: Primer 951216

<400> SEQUENCE: 22
cgccgcggta ttctgcag                                          18

<210> SEQ ID NO 23
<211> LENGTH: 50
<212> TYPE: DNA
<213> ORGANISM: Artificial Sequence
<220> FEATURE:
<223> OTHER INFORMATION: Primer Tal 1

<400> SEQUENCE: 23
caatataaac gacggtaccc ggagatctc caccatggcg tccctcgttg         50

<210> SEQ ID NO 24
<211> LENGTH: 44
<212> TYPE: DNA
<213> ORGANISM: Artificial Sequence
<220> FEATURE:
<223> OTHER INFORMATION: Tal 4

<400> SEQUENCE: 24
ctaattacat catgcggccc ctagatcac tgccaactat cgtc              44

<210> SEQ ID NO 25
<211> LENGTH: 21
<212> TYPE: DNA
<213> ORGANISM: Artificial Sequence
<220> FEATURE:
<223> OTHER INFORMATION: Primer Tal 5

<400> SEQUENCE: 25
aatttgggtc gctcctgctc                                        21

<210> SEQ ID NO 26
<211> LENGTH: 40
<212> TYPE: DNA
<213> ORGANISM: Artificial Sequence
<220> FEATURE:
<223> OTHER INFORMATION: Tal 6

-continued

```
<400> SEQUENCE: 26
cgagcaggag cgacccaaat atttctact cctggacacg                              40

<210> SEQ ID NO 27
<211> LENGTH: 20
<212> TYPE: DNA
<213> ORGANISM: Artificial Sequence
<220> FEATURE:
<223> OTHER INFORMATION: Tal 7

<400> SEQUENCE: 27
gatgagatag ttcgcatacg                                                   20

<210> SEQ ID NO 28
<211> LENGTH: 43
<212> TYPE: DNA
<213> ORGANISM: Artificial Sequence
<220> FEATURE:
<223> OTHER INFORMATION: Tal 8

<400> SEQUENCE: 28
cgtatgcgaa ctatctcatc acaacggcg aggcttcgac tgc                          43

<210> SEQ ID NO 29
<211> LENGTH: 20
<212> TYPE: DNA
<213> ORGANISM: Artificial Sequence
<220> FEATURE:
<223> OTHER INFORMATION: Tal 9

<400> SEQUENCE: 29
cgaaggtgga tgagttccag                                                   20

<210> SEQ ID NO 30
<211> LENGTH: 42
<212> TYPE: DNA
<213> ORGANISM: Artificial Sequence
<220> FEATURE:
<223> OTHER INFORMATION: Tal 10

<400> SEQUENCE: 30
ctggaactca tccaccttcg cctctggga agaagtagaa gg                           42

<210> SEQ ID NO 31
<211> LENGTH: 21
<212> TYPE: DNA
<213> ORGANISM: Artificial Sequence
<220> FEATURE:
<223> OTHER INFORMATION: Tal 11

<400> SEQUENCE: 31
gacaatactc agatatccat                                                   21

<210> SEQ ID NO 32
<211> LENGTH: 43
<212> TYPE: DNA
<213> ORGANISM: Artificial Sequence
<220> FEATURE:
<223> OTHER INFORMATION: Tal 12

<400> SEQUENCE: 32
gatggatatc tgagtattgt gagaaatat actccctcag acg                          43

<210> SEQ ID NO 33
```

-continued

<211> LENGTH: 2748
<212> TYPE: DNA
<213> ORGANISM: Talaromyces emersonii

<400> SEQUENCE: 33

```
acgagatgtg tatatactgt gaaccaaact agatgatgtc agttatgctg gtctgagaac    60
tcatagaagc ccttgaaaat accccaagct agcactccaa ccctaactct gttgctctac   120
tagatcaaga cgagtactct gattgagctg caggcttgga atatatgatt agcagaaaaa   180
gggttaaaac ttgtatgaca atcagtttgt cagtactccg tagtgatgcc atgtctatag   240
agtcgacact aaggcagcat gtgaatgagt cggaaatgaa aggaagcaga ttccttaaca   300
gtcatgttct ccgtgcctgc atccccacgt cacctgcaaa gatgcgacgc tactccacac   360
cggcgccttg atgtctgctg ttcctggcct agtggagccc catgcgctgc tagctcgtgg   420
tcttcgaata aatcagaata aaaaacggag taattaattg cgcccgcaac aaactaagca   480
atgtaactca atgccaagct tccgctgatg ctcttgacat ctccgtagtg gcttctttcg   540
taatttcaga cgtatatata gtagtaatgc ccagcaggcc gggataatga tggggatttc   600
tgaactctca gcttccgtac gctgaacagt ttgcttgcgt tgtcaaccat ggcgtccctc   660
gttgctggcg ctctctgcat cctgggcctg acgcctgctg catttgcacg agcgcccgtt   720
gcagcgcgag ccaccggttc cctggactcc tttctcgcaa ccgaaactcc aattgccctc   780
caaggcgtgc tgaacaacat cgggcccaat ggtgctgatg tggcaggagc aagcgccggc   840
attgtggttg ccagtccgag caggagcgac ccaaattgta ggttctttcc caccagaaat   900
tacttattta aatcagccct ctgacaggtt gaagatttct actcctggac acgtgacgca   960
gcgctcacgg ccaaatacct cgtcgacgcc ttcatcgcgg caacaaggac ctagagcag  1020
accatccagc agtacatcag cgcgcaggcg aaggtgcaaa ctatctccaa tccgtccgga  1080
gatttatcca ccggtggctt aggtgagccc aagttcaatg tgaatgagac ggcttttacc  1140
gggccctggg gtcgtccaca gagggacgga ccagcgttga gagcgacggc cctcattgcg  1200
tatgcgaact atctcatcgt aagcttctgc tcgctgccct tctctctgct cgtatgctaa  1260
gtagtcctgt caggacaacg gcgaggcttc gactgccgat gagatcatct ggccgattgt  1320
ccagaatgat ctgtcctaca tcacccaata ctggaactca tccaccttcg gtaggcaaat  1380
gaatattccc gacacagcgt ggtactaatt tgattcagac ctctgggaag aagtagaagg  1440
atcctcattc ttcacaaccg ccgtgcaaca ccgcgccctg gtcgaaggca atgcactggc  1500
aacaaggctg aaccacacgt gctccaactg cgtctctcag gccctcagg tcctgtgttt  1560
cctgcagtca tactgaccg gatcgtatgt tctggccaac tttggtggca gcggtcgttc  1620
cggcaaggac gtgaattcga ttctgggcag catccacacc tttgatcccg ccggaggctg  1680
tgacgactcg accttccagc cgtgttcggc ccgtgccttg gcaaatcaca aggtggtcac  1740
cgactcgttc cggagtatct atgcgatcaa ctcaggcatc gcagagggat ctgccgtggc  1800
agtcggccgc taccctgagg atgtctacca gggcgggaac ccctggtacc tggccacagc  1860
agcggctgca gagcagcttt acgacgccat ctaccagtgg aagaagatcg gctcgataag  1920
tatcacggac gttagtctgc cattttttcca ggatatctac ccttctgccg gtgtgggcac  1980
ctataactct ggctccacga ctttcaacga catcatctcg gccgtccaga cgtatggtga  2040
tggatatctg agtattgtcg tacgttttgc cttagattct caggtgtaaa gaaaaaaatg  2100
gaactaactc agttctagga gaaatatact ccctcagacg gctctcttac cgaacaattc  2160
tcccgtacag acggcactcc gctttctgcc tctgccctga cttggtcgta cgcttctctc  2220
```

-continued

```
ctaaccgctt cggcccgcag acagtccgtc gtccctgctt cctggggcga agctccgca    2280 agcagcgtcc ctgccgtctg ctctgccacc tctgccacgg gcccatacag cacggctacc   2340
aacaccgtct ggccaagctc tggctctggc agctcaacaa ccaccagtag cgccccatgc   2400
accactccta cctctgtggc tgtgaccttc gacgaaatcg tcagcaccag ttacggggag   2460
acaatctacc tggccggctc gatccccgag ctgggcaact ggtccacggc cagcgcgatc   2520
cccctccgcg cggatgctta caccaacagc aacccgctct ggtacgtgac cgtcaatctg   2580 cccctggca ccagcttcga gtacaagttc ttcaagaacc agacggacgg gaccatcgtc    2640
tgggaagacg acccgaaccg gtcgtacacg gtcccagcgt actgtgggca gactaccgcc   2700
attcttgacg atagttggca gtgagataac atccaccctt ctgttttta               2748
```

<210> SEQ ID NO 34
<211> LENGTH: 618
<212> TYPE: PRT
<213> ORGANISM: Talaromyces emersonii

<400> SEQUENCE: 34

```
Met Ala Ser Leu Val Ala Gly Ala Leu Cys Ile Leu Gly Leu Thr Pro
 1               5                  10                  15

Ala Ala Phe Ala Arg Ala Pro Val Ala Ala Arg Ala Thr Gly Ser Leu
            20                  25                  30

Asp Ser Phe Leu Ala Thr Glu Thr Pro Ile Ala Leu Gln Gly Val Leu
        35                  40                  45

Asn Asn Ile Gly Pro Asn Gly Ala Asp Val Ala Gly Ala Ser Ala Gly
    50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Gln Tyr Ile Ser
            100                 105                 110

Ala Gln Ala Lys Val Gln Thr Ile Ser Asn Pro Ser Gly Asp Leu Ser
        115                 120                 125

Thr Gly Gly Leu Gly Glu Pro Lys Phe Asn Val Asn Glu Thr Ala Phe
    130                 135                 140

Thr Gly Pro Trp Gly Arg Pro Gln Arg Asp Gly Pro Ala Leu Arg Ala
145                 150                 155                 160

Thr Ala Leu Ile Ala Tyr Ala Asn Tyr Leu Ile Asp Asn Gly Glu Ala
                165                 170                 175

Ser Thr Ala Asp Glu Ile Ile Trp Pro Ile Val Gln Asn Asp Leu Ser
            180                 185                 190

Tyr Ile Thr Gln Tyr Trp Asn Ser Ser Thr Phe Asp Leu Trp Glu Glu
        195                 200                 205

Val Glu Gly Ser Ser Phe Phe Thr Thr Ala Val Gln His Arg Ala Leu
    210                 215                 220

Val Glu Gly Asn Ala Leu Ala Thr Arg Leu Asn His Thr Cys Ser Asn
225                 230                 235                 240

Cys Val Ser Gln Ala Pro Gln Val Leu Cys Phe Leu Gln Ser Tyr Trp
                245                 250                 255

Thr Gly Ser Tyr Val Leu Ala Asn Phe Gly Gly Ser Gly Arg Ser Gly
            260                 265                 270

Lys Asp Val Asn Ser Ile Leu Gly Ser Ile His Thr Phe Asp Pro Ala
```

-continued

```
                275                 280                 285
Gly Gly Cys Asp Asp Ser Thr Phe Gln Pro Cys Ser Ala Arg Ala Leu
        290                 295                 300
Ala Asn His Lys Val Val Thr Asp Ser Phe Arg Ser Ile Tyr Ala Ile
305                 310                 315                 320
Asn Ser Gly Ile Ala Glu Gly Ser Ala Val Ala Val Gly Arg Tyr Pro
                325                 330                 335
Glu Asp Val Tyr Gln Gly Gly Asn Pro Trp Tyr Leu Ala Thr Ala Ala
                340                 345                 350
Ala Ala Glu Gln Leu Tyr Asp Ala Ile Tyr Gln Trp Lys Lys Ile Gly
        355                 360                 365
Ser Ile Ser Ile Thr Asp Val Ser Leu Pro Phe Phe Gln Asp Ile Tyr
        370                 375                 380
Pro Ser Ala Ala Val Gly Thr Tyr Asn Ser Gly Ser Thr Thr Phe Asn
385                 390                 395                 400
Asp Ile Ile Ser Ala Val Gln Thr Tyr Gly Asp Gly Tyr Leu Ser Ile
                405                 410                 415
Val Glu Lys Tyr Thr Pro Ser Asp Gly Ser Leu Thr Glu Gln Phe Ser
        420                 425                 430
Arg Thr Asp Gly Thr Pro Leu Ser Ala Ser Ala Leu Thr Trp Ser Tyr
        435                 440                 445
Ala Ser Leu Leu Thr Ala Ser Ala Arg Arg Gln Ser Val Val Pro Ala
        450                 455                 460
Ser Trp Gly Glu Ser Ser Ala Ser Ser Val Pro Ala Val Cys Ser Ala
465                 470                 475                 480
Thr Ser Ala Thr Gly Pro Tyr Ser Thr Ala Thr Asn Thr Val Trp Pro
                485                 490                 495
Ser Ser Gly Ser Gly Ser Ser Thr Thr Thr Ser Ser Ala Pro Cys Thr
                500                 505                 510
Thr Pro Thr Ser Val Ala Val Thr Phe Asp Glu Ile Val Ser Thr Ser
        515                 520                 525
Tyr Gly Glu Thr Ile Tyr Leu Ala Gly Ser Ile Pro Glu Leu Gly Asn
        530                 535                 540
Trp Ser Thr Ala Ser Ala Ile Pro Leu Arg Ala Asp Ala Tyr Thr Asn
545                 550                 555                 560
Ser Asn Pro Leu Trp Tyr Val Thr Val Asn Leu Pro Pro Gly Thr Ser
                565                 570                 575
Phe Glu Tyr Lys Phe Phe Lys Asn Gln Thr Asp Gly Thr Ile Val Trp
            580                 585                 590
Glu Asp Asp Pro Asn Arg Ser Tyr Thr Val Pro Ala Tyr Cys Gly Gln
        595                 600                 605
Thr Thr Ala Ile Leu Asp Asp Ser Trp Gln
610                 615
```